US012605433B2

(12) United States Patent
Lee et al.

(10) Patent No.: US 12,605,433 B2
(45) Date of Patent: Apr. 21, 2026

(54) ANTIBODY SPECIFICALLY BINDING TO PTK7 AND USE THEREOF

(71) Applicants: UIF (University Industry Foundation), Yonsei University, Seoul (KR); OSONG MEDICAL INNOVATION FOUNDATION, Chungcheongbuk-do (KR)

(72) Inventors: Seung Taek Lee, Seoul (KR); Won Sik Shin, Seoul (KR); Si Won Oh, Gyeonggi-do (KR); So Young Choi, Sejong-si (KR); Se Ra Lee, Sejong-si (KR); So Ra Park, Chungcheongbuk-do (KR)

(73) Assignees: UIF (University Industry Foundation), Yonsei University, Seoul (KR); OSONG MEDICAL INNOVATION FOUNDATION, Chungcheongbuk-do (KR)

( * ) Notice: Subject to any disclaimer, the term of this patent is extended or adjusted under 35 U.S.C. 154(b) by 747 days.

(21) Appl. No.: 18/016,100

(22) PCT Filed: Jul. 16, 2021

(86) PCT No.: PCT/KR2021/009208
§ 371 (c)(1),
(2) Date: Jan. 13, 2023

(87) PCT Pub. No.: WO2022/015113
PCT Pub. Date: Jan. 20, 2022

(65) Prior Publication Data
US 2025/0340670 A1 Nov. 6, 2025

(30) Foreign Application Priority Data

Jul. 16, 2020 (KR) ........................ 10-2020-0088476
Jul. 16, 2021 (KR) ........................ 10-2021-0093285

(51) Int. Cl.
*C07K 16/40* (2006.01)
*A61K 39/00* (2006.01)
*A61P 9/00* (2006.01)
*A61P 35/00* (2006.01)

(52) U.S. Cl.
CPC ............... *A61K 39/00* (2013.01); *A61P 9/00* (2018.01); *A61P 35/00* (2018.01); *C07K 16/40* (2013.01); *C07K 2317/622* (2013.01)

(58) Field of Classification Search
None
See application file for complete search history.

(56) References Cited

U.S. PATENT DOCUMENTS 9,102,738 B2 8/2015 Terrett et al.
2018/0162952 A1 6/2018 Foord et al.

FOREIGN PATENT DOCUMENTS

KR      10-2008-0082660 A    9/2008
KR      10-2009-0099471 A    9/2009
KR      10-2010-0101124 A    9/2010
KR      10-2014-0018905 A    2/2014
KR         10-2238032 B1    4/2021
WO    WO-2007067730 A2 *  6/2007    .............. A61P 35/02
WO    WO-2013/006490 A2    1/2013

OTHER PUBLICATIONS

Office Action from corresponding Korean Application No. 10-2021-0093285, Dated Jul. 19, 2023.
Won-Sik Shin et al., "Soluble PTK7 inhibits tube formation, migration, and invasion of endothelial cells and angiogenesis", Biochemical and Biophysical Research Communications 371 (2008) 793-798.
Won-Sik Shin et al., "Biphasic regulation of tumorigenesis by PTK7 expression level in esophageal squamous cell carcinoma", Scientific Reports 2018.
International Search Report from corresponding PCT Application No. PCT/KR2021/009208, dated Nov. 11, 2021.

* cited by examiner

*Primary Examiner* — Sharon X Wen

(74) *Attorney, Agent, or Firm* — Harness, Dickey & Pierce, P.L.C.

(57) ABSTRACT

Proposed are antibodies specifically binding to PTK7 and a use thereof and, more particularly, PTK7 neutralizing antibodies specifically binding to PTK7 to inhibit PTK function, and a use thereof for inhibiting angiogenesis, cell growth, cell migration, and cell invasion. The human PTK7 neutralizing monoclonal antibodies have been found to independently exhibit an effective inhibitory effect on cancer cell growth, migration, invasion in esophageal squamous cell carcinoma and triple-negative breast cancer, and angiogenesis. Therefore, the human PTK7 neutralizing monoclonal antibodies can be applied to various PTK7-positive carcinomas and angiogenic diseases, and can be further developed as a targeted drug therapy for intractable cancers and angiogenic diseases to be used as a core global treatment drug for the same.

16 Claims, 15 Drawing Sheets

Specification includes a Sequence Listing.

FIG. 12

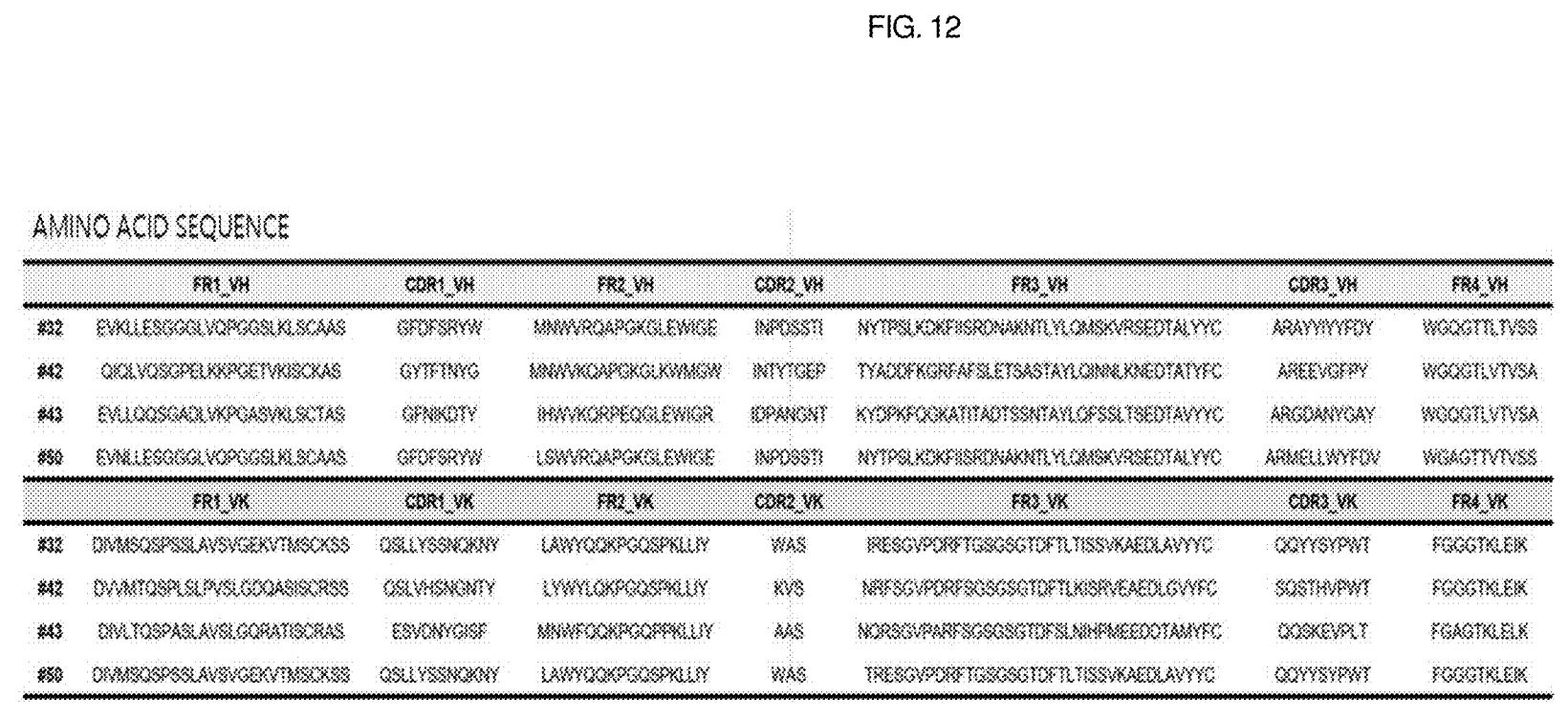

AMINO ACID SEQUENCE

| | FR1_VH | CDR1_VH | FR2_VH | CDR2_VH | FR3_VH | CDR3_VH | FR4_VH |
|---|---|---|---|---|---|---|---|
| #32 | | | | | | | |
| #42 | | | | | | | |
| #43 | | | | | | | |
| #50 | | | | | | | |

| | FR1_VK | CDR1_VK | FR2_VK | CDR2_VK | FR3_VK | CDR3_VK | FR4_VK |
|---|---|---|---|---|---|---|---|
| #32 | | | | | | | |
| #42 | | | | | | | |
| #43 | | | | | | | |
| #50 | | | | | | | |

```
                          SEQUENCE LISTING

<160> NUMBER OF SEQ ID NOS: 44

<210> SEQ ID NO 1
<211> LENGTH: 8
<212> TYPE: PRT
<213> ORGANISM: Artificial Sequence
<220> FEATURE:
<223> OTHER INFORMATION: #32_CDR1_VH

<400> SEQUENCE: 1

Gly Phe Asp Phe Ser Arg Tyr Trp
1               5

<210> SEQ ID NO 2
<211> LENGTH: 8
<212> TYPE: PRT
<213> ORGANISM: Artificial Sequence
<220> FEATURE:
<223> OTHER INFORMATION: #32_CDR2_VH

<400> SEQUENCE: 2

Ile Asn Pro Asp Ser Ser Thr Ile
1               5

<210> SEQ ID NO 3
<211> LENGTH: 11
<212> TYPE: PRT
<213> ORGANISM: Artificial Sequence
<220> FEATURE:
<223> OTHER INFORMATION: #32_CDR3_VH

<400> SEQUENCE: 3

Ala Arg Ala Tyr Tyr Ile Tyr Tyr Phe Asp Tyr
1               5                   10

<210> SEQ ID NO 4
<211> LENGTH: 12
<212> TYPE: PRT
<213> ORGANISM: Artificial Sequence
<220> FEATURE:
<223> OTHER INFORMATION: #32_CDR1_VL

<400> SEQUENCE: 4
```

```
Gln Ser Leu Leu Tyr Ser Ser Asn Gln Lys Asn Tyr
1               5                   10

<210> SEQ ID NO 5
<211> LENGTH: 3
<212> TYPE: PRT
<213> ORGANISM: Artificial Sequence
<220> FEATURE:
<223> OTHER INFORMATION: #32_CDR2_VL

<400> SEQUENCE: 5

Trp Ala Ser
1

<210> SEQ ID NO 6
<211> LENGTH: 9
<212> TYPE: PRT
<213> ORGANISM: Artificial Sequence
<220> FEATURE:
<223> OTHER INFORMATION: #32_CDR3_VL

<400> SEQUENCE: 6

Gln Gln Tyr Tyr Ser Tyr Pro Trp Thr
1               5

<210> SEQ ID NO 7
<211> LENGTH: 8
<212> TYPE: PRT
<213> ORGANISM: Artificial Sequence
<220> FEATURE:
<223> OTHER INFORMATION: #42_CDR1_VH

<400> SEQUENCE: 7

Gly Tyr Thr Phe Thr Asn Tyr Gly
1               5

<210> SEQ ID NO 8
<211> LENGTH: 8
<212> TYPE: PRT
<213> ORGANISM: Artificial Sequence
<220> FEATURE:
<223> OTHER INFORMATION: #42_CDR2_VH

<400> SEQUENCE: 8

Ile Asn Thr Tyr Thr Gly Glu Pro
1               5

<210> SEQ ID NO 9
<211> LENGTH: 9
<212> TYPE: PRT
<213> ORGANISM: Artificial Sequence
<220> FEATURE:
<223> OTHER INFORMATION: #42_CDR3_VH

<400> SEQUENCE: 9

Ala Arg Glu Glu Val Gly Phe Pro Tyr
1               5

<210> SEQ ID NO 10
<211> LENGTH: 11
<212> TYPE: PRT
<213> ORGANISM: Artificial Sequence
<220> FEATURE:
<223> OTHER INFORMATION: #42_CDR1_VL

<400> SEQUENCE: 10

Gln Ser Leu Val His Ser Asn Gly Asn Thr Tyr
```

-continued

```
1               5               10

<210> SEQ ID NO 11
<211> LENGTH: 3
<212> TYPE: PRT
<213> ORGANISM: Artificial Sequence
<220> FEATURE:
<223> OTHER INFORMATION: #42_CDR2_VL

<400> SEQUENCE: 11

Lys Val Ser
1

<210> SEQ ID NO 12
<211> LENGTH: 9
<212> TYPE: PRT
<213> ORGANISM: Artificial Sequence
<220> FEATURE:
<223> OTHER INFORMATION: #42_CDR3_VL

<400> SEQUENCE: 12

Ser Gln Ser Thr His Val Pro Trp Thr
1               5

<210> SEQ ID NO 13
<211> LENGTH: 8
<212> TYPE: PRT
<213> ORGANISM: Artificial Sequence
<220> FEATURE:
<223> OTHER INFORMATION: #43_CDR1_VH

<400> SEQUENCE: 13

Gly Phe Asn Ile Lys Asp Thr Tyr
1               5

<210> SEQ ID NO 14
<211> LENGTH: 8
<212> TYPE: PRT
<213> ORGANISM: Artificial Sequence
<220> FEATURE:
<223> OTHER INFORMATION: #43_CDR2_VH

<400> SEQUENCE: 14

Ile Asp Pro Ala Asn Gly Asn Thr
1               5

<210> SEQ ID NO 15
<211> LENGTH: 10
<212> TYPE: PRT
<213> ORGANISM: Artificial Sequence
<220> FEATURE:
<223> OTHER INFORMATION: #43_CDR3_VH

<400> SEQUENCE: 15

Ala Arg Gly Asp Ala Asn Tyr Gly Ala Tyr
1               5               10

<210> SEQ ID NO 16
<211> LENGTH: 10
<212> TYPE: PRT
<213> ORGANISM: Artificial Sequence
<220> FEATURE:
<223> OTHER INFORMATION: #43_CDR1_VL

<400> SEQUENCE: 16

Glu Ser Val Asp Asn Tyr Gly Ile Ser Phe
1               5               10
```

-continued

```
<210> SEQ ID NO 17
<211> LENGTH: 3
<212> TYPE: PRT
<213> ORGANISM: Artificial Sequence
<220> FEATURE:
<223> OTHER INFORMATION: #43_CDR2_VL

<400> SEQUENCE: 17

Ala Ala Ser
1

<210> SEQ ID NO 18
<211> LENGTH: 9
<212> TYPE: PRT
<213> ORGANISM: Artificial Sequence
<220> FEATURE:
<223> OTHER INFORMATION: #43_CDR3_VL

<400> SEQUENCE: 18

Gln Gln Ser Lys Glu Val Pro Leu Thr
1               5

<210> SEQ ID NO 19
<211> LENGTH: 8
<212> TYPE: PRT
<213> ORGANISM: Artificial Sequence
<220> FEATURE:
<223> OTHER INFORMATION: #50_CDR1_VH

<400> SEQUENCE: 19

Gly Phe Asp Phe Ser Arg Tyr Trp
1               5

<210> SEQ ID NO 20
<211> LENGTH: 8
<212> TYPE: PRT
<213> ORGANISM: Artificial Sequence
<220> FEATURE:
<223> OTHER INFORMATION: #50_CDR2_VH

<400> SEQUENCE: 20

Ile Asn Pro Asp Ser Ser Thr Ile
1               5

<210> SEQ ID NO 21
<211> LENGTH: 11
<212> TYPE: PRT
<213> ORGANISM: Artificial Sequence
<220> FEATURE:
<223> OTHER INFORMATION: #50_CDR3_VH

<400> SEQUENCE: 21

Ala Arg Met Glu Leu Leu Trp Tyr Phe Asp Val
1               5                   10

<210> SEQ ID NO 22
<211> LENGTH: 12
<212> TYPE: PRT
<213> ORGANISM: Artificial Sequence
<220> FEATURE:
<223> OTHER INFORMATION: #50_CDR1_VL

<400> SEQUENCE: 22

Gln Ser Leu Leu Tyr Ser Ser Asn Gln Lys Asn Tyr
1               5                   10
```

```
<210> SEQ ID NO 23
<211> LENGTH: 3
<212> TYPE: PRT
<213> ORGANISM: Artificial Sequence
<220> FEATURE:
<223> OTHER INFORMATION: #50_CDR2_VL

<400> SEQUENCE: 23

Trp Ala Ser
1

<210> SEQ ID NO 24
<211> LENGTH: 9
<212> TYPE: PRT
<213> ORGANISM: Artificial Sequence
<220> FEATURE:
<223> OTHER INFORMATION: #50_CDR3_VL

<400> SEQUENCE: 24

Gln Gln Tyr Tyr Ser Tyr Pro Trp Thr
1               5

<210> SEQ ID NO 25
<211> LENGTH: 118
<212> TYPE: PRT
<213> ORGANISM: Artificial Sequence
<220> FEATURE:
<223> OTHER INFORMATION: #32_VH

<400> SEQUENCE: 25

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg Ala Tyr Tyr Ile Tyr Tyr Phe Asp Tyr Trp Gly Gln Gly Thr
            100                 105                 110

Thr Leu Thr Val Ser Ser
        115

<210> SEQ ID NO 26
<211> LENGTH: 113
<212> TYPE: PRT
<213> ORGANISM: Artificial Sequence
<220> FEATURE:
<223> OTHER INFORMATION: #32_VL

<400> SEQUENCE: 26

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45
```

```
Ser Pro Lys Leu Leu Ile Tyr Trp Ala Ser Ile Arg Glu Ser Gly Val
50              55                  60

Pro Asp Arg Phe Thr Gly Ser Gly Ser Gly Thr Asp Phe Thr Leu Thr
65              70                  75                  80

Ile Ser Ser Val Lys Ala Glu Asp Leu Ala Val Tyr Tyr Cys Gln Gln
                85                  90                  95

Tyr Tyr Ser Tyr Pro Trp Thr Phe Gly Gly Gly Thr Lys Leu Glu Ile
            100                 105                 110

Lys

<210> SEQ ID NO 27
<211> LENGTH: 116
<212> TYPE: PRT
<213> ORGANISM: Artificial Sequence
<220> FEATURE:
<223> OTHER INFORMATION: #42_VH

<400> SEQUENCE: 27

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
                20                  25                  30

Gly Met Asn Trp Val Lys Gln Ala Pro Gly Lys Gly Leu Lys Trp Met
            35                  40                  45

Gly Trp Ile Asn Thr Tyr Thr Gly Glu Pro Thr Tyr Ala Asp Asp Phe
        50                  55                  60

Lys Gly Arg Phe Ala Phe Ser Leu Glu Thr Ser Ala Ser Thr Ala Tyr
65              70                  75                  80

Leu Gln Ile Asn Asn Leu Lys Asn Glu Asp Thr Ala Thr Tyr Phe Cys
                85                  90                  95

Ala Arg Glu Glu Val Gly Phe Pro Tyr Trp Gly Gln Gly Thr Leu Val
            100                 105                 110

Thr Val Ser Ala
        115

<210> SEQ ID NO 28
<211> LENGTH: 112
<212> TYPE: PRT
<213> ORGANISM: Artificial Sequence
<220> FEATURE:
<223> OTHER INFORMATION: #42_VL

<400> SEQUENCE: 28

Asp Val Val Met Thr Gln Ser Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu Tyr Trp Tyr Leu Gln Lys Pro Gly Gln Ser
            35                  40                  45

Pro Lys Leu Leu Ile Tyr Lys Val Ser Asn Arg Phe Ser Gly Val Pro
50              55                  60

Asp Arg Phe Ser Gly Ser Gly Ser Gly Thr Asp Phe Thr Leu Lys Ile
65              70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110
```

```
<210> SEQ ID NO 29
<211> LENGTH: 117
<212> TYPE: PRT
<213> ORGANISM: Artificial Sequence
<220> FEATURE:
<223> OTHER INFORMATION: #43_VH

<400> SEQUENCE: 29

Glu Val Leu Leu Gln Gln Ser Gly Ala Asp Leu Val Lys Pro Gly Ala
1               5                   10                  15

Ser Val Lys Leu Ser Cys Thr Ala Ser Gly Phe Asn Ile Lys Asp Thr
                20                  25                  30

Tyr Ile His Trp Val Lys Gln Arg Pro Glu Gln Gly Leu Glu Trp Ile
            35                  40                  45

Gly Arg Ile Asp Pro Ala Asn Gly Asn Thr Lys Tyr Asp Pro Lys Phe
        50                  55                  60

Gln Gly Lys Ala Thr Ile Thr Ala Asp Thr Ser Ser Asn Thr Ala Tyr
65                  70                  75                  80

Leu Gln Phe Ser Ser Leu Thr Ser Glu Asp Thr Ala Val Tyr Tyr Cys
                85                  90                  95

Ala Arg Gly Asp Ala Asn Tyr Gly Ala Tyr Trp Gly Gln Gly Thr Leu
            100                 105                 110

Val Thr Val Ser Ala
        115

<210> SEQ ID NO 30
<211> LENGTH: 111
<212> TYPE: PRT
<213> ORGANISM: Artificial Sequence
<220> FEATURE:
<223> OTHER INFORMATION: #43_VL

<400> SEQUENCE: 30

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
                20                  25                  30

Gly Ile Ser Phe Met Asn Trp Phe Gln Gln Lys Pro Gly Gln Pro Pro
            35                  40                  45

Lys Leu Leu Ile Tyr Ala Ala Ser Asn Gln Arg Ser Gly Val Pro Ala
        50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Leu Thr Phe Gly Ala Gly Thr Lys Leu Glu Leu Lys
            100                 105                 110

<210> SEQ ID NO 31
<211> LENGTH: 118
<212> TYPE: PRT
<213> ORGANISM: Artificial Sequence
<220> FEATURE:
<223> OTHER INFORMATION: #50_VH

<400> SEQUENCE: 31

Glu Val Asn Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
```

```
                20              25              30

Trp Leu Ser Trp Val Arg Gln Ala Pro Gly Lys Gly Leu Glu Trp Ile
        35              40              45

Gly Glu Ile Asn Pro Asp Ser Ser Thr Ile Asn Tyr Thr Pro Ser Leu
    50              55              60

Lys Asp Lys Phe Ile Ile Ser Arg Asp Asn Ala Lys Asn Thr Leu Tyr
65              70              75              80

Leu Gln Met Ser Lys Val Arg Ser Glu Asp Thr Ala Leu Tyr Tyr Cys
                85              90              95

Ala Arg Met Glu Leu Leu Trp Tyr Phe Asp Val Trp Gly Ala Gly Thr
            100             105             110

Thr Val Thr Val Ser Ser
            115

<210> SEQ ID NO 32
<211> LENGTH: 113
<212> TYPE: PRT
<213> ORGANISM: Artificial Sequence
<220> FEATURE:
<223> OTHER INFORMATION: #50_VL

<400> SEQUENCE: 32

Asp Ile Val Met Ser Gln Ser Pro Ser Ser Leu Ala Val Ser Val Gly
1               5               10              15

Glu Lys Val Thr Met Ser Cys Lys Ser Ser Gln Ser Leu Leu Tyr Ser
                20              25              30

Ser Asn Gln Lys Asn Tyr Leu Ala Trp Tyr Gln Gln Lys Pro Gly Gln
        35              40              45

Ser Pro Lys Leu Leu Ile Tyr Trp Ala Ser Thr Arg Glu Ser Gly Val
    50              55              60

Pro Asp Arg Phe Thr Gly Ser Gly Ser Gly Thr Asp Phe Thr Leu Thr
65              70              75              80

Ile Ser Ser Val Lys Ala Glu Asp Leu Ala Val Tyr Tyr Cys Gln Gln
                85              90              95

Tyr Tyr Ser Tyr Pro Trp Thr Phe Gly Gly Gly Thr Lys Leu Glu Ile
            100             105             110

Lys

<210> SEQ ID NO 33
<211> LENGTH: 354
<212> TYPE: DNA
<213> ORGANISM: Artificial Sequence
<220> FEATURE:
<223> OTHER INFORMATION: #32_VH

<400> SEQUENCE: 33
gaggtgaagc ttctcgagtc tggaggtggc ctggtgcagc ctggaggatc cctgaaactc     60
tcctgtgcag cctcaggatt cgattttagt agatactgga tgaattgggt ccggcaggct    120
ccagggaaag ggctagaatg gattggagaa attaatccag atagcagtac gataaactat    180
acgccatctc taaaggataa attcatcatc tccagagaca acgccaaaaa tacgctgtac    240
ctgcaaatga gcaaagtgag atctgaggac acagcccttt attactgtgc aagagcctac    300
tatatatact actttgacta ctggggccaa ggcaccactc tcacagtctc ctca          354

<210> SEQ ID NO 34
<211> LENGTH: 339
<212> TYPE: DNA
```

```
<213> ORGANISM: Artificial Sequence
<220> FEATURE:
<223> OTHER INFORMATION: #32_VL

<400> SEQUENCE: 34
gacattgtga tgtcacagtc tccatcctcc ctagctgtgt cagttggaga gaaggttact      60
atgagttgca agtccagtca gagccttta tatagtagca atcaaaagaa ctacttggcc     120
tggtaccagc agaaaccagg gcagtctcct aaactgctga tttactgggc atccattagg     180
gaatctgggg tccctgatcg cttcacaggc agtggatctg ggacagattt cactctcacc     240
atcagcagtg tgaaggctga agacctggca gtttattact gtcagcaata ttatagctat     300
ccgtggacgt tcggtggagg caccaagctg gaaatcaaa                             339

<210> SEQ ID NO 35
<211> LENGTH: 348
<212> TYPE: DNA
<213> ORGANISM: Artificial Sequence
<220> FEATURE:
<223> OTHER INFORMATION: #42_VH

<400> SEQUENCE: 35
cagatccagt tggtgcagtc tggacctgag ctgaagaagc ctggagagac agtcaagatc      60
tcctgcaagg cttctgggta taccttcaca aactatggaa tgaactgggt gaagcaggct     120
ccaggaaagg gtttaaagtg gatgggctgg ataaacacct acactggaga gccaacatat     180
gctgatgact tcaagggacg gtttgccttc tctttggaaa cctctgccag cactgcctat     240
ttgcagatca caacctcaa aaatgaggac acggctacat atttctgtgc aagagaggag     300
gtaggatttc cttactgggg ccaagggact ctggtcactg tctctgca                 348

<210> SEQ ID NO 36
<211> LENGTH: 336
<212> TYPE: DNA
<213> ORGANISM: Artificial Sequence
<220> FEATURE:
<223> OTHER INFORMATION: #42_VL

<400> SEQUENCE: 36
gatgttgtga tgacccaaag tccactctcc ctgcctgtca gtcttggaga tcaagcctcc      60
atctcttgca gatctagtca gagccttgta cacagtaatg gaaacaccta tttatactgg     120
tacctgcaga agccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaagtac acatgttccg     300
tggacgttcg gtggaggcac caagctggaa atcaaa                               336

<210> SEQ ID NO 37
<211> LENGTH: 351
<212> TYPE: DNA
<213> ORGANISM: Artificial Sequence
<220> FEATURE:
<223> OTHER INFORMATION: #43_VH

<400> SEQUENCE: 37
gaggttcttc tgcagcagtc tggggcagac cttgtgaagc caggggcctc agtcaagttg      60
tcctgcacag cttctggctt caacattaaa gacacctata tacactgggt gaagcagagg     120
cctgaacagg gcctggagtg gattggaagg attgatcctg cgaatggtaa tactaaatat     180
gacccgaagt tccagggcaa ggccactata acagcagaca tcctccaa cacagcctac     240
```

-continued

```
ctgcagttca gcagcctgac atctgaggac actgccgtct attactgtgc tagaggggat      300
gctaactacg gtgcttactg gggccaaggg actctggtca ctgtctctgc a              351

<210> SEQ ID NO 38
<211> LENGTH: 333
<212> TYPE: DNA
<213> ORGANISM: Artificial Sequence
<220> FEATURE:
<223> OTHER INFORMATION: #43_VL

<400> SEQUENCE: 38
gacattgtgc tgacccaatc tccagcttct ttggctgtgt ctctagggca gagggccacc       60
atctcctgca gagccagcga aagtgttgat aattatggca ttagtttat gaactggttc      120 caacagaaac caggacagcc acccaaactc ctcatctatg ctgcatccaa ccaaagatcc      180
ggggtccctg ccaggtttag tggcagtggg tctgggacag acttcagcct caacatccat      240
cctatggagg aggatgatac tgcaatgtat ttctgtcagc aaagtaagga ggttccgctc      300
acgttcggtg ctgggaccaa gctggagctg aaa                                  333

<210> SEQ ID NO 39
<211> LENGTH: 354
<212> TYPE: DNA
<213> ORGANISM: Artificial Sequence
<220> FEATURE:
<223> OTHER INFORMATION: #50_VH

<400> SEQUENCE: 39
gaggtgaatc ttctcgagtc tggaggtggc ctggtgcagc ctggaggatc cctgaaactc       60
tcctgtgcag cctcaggatt cgattttagt agatactggc tgagttgggt ccggcaggct      120
ccagggaaag ggctagaatg gattggagaa attaatccag atagcagtac gataaactat      180
acgccatctc taaaggataa attcatcatc tccagagaca cgccaaaaa tacgctgtac      240 ctgcaaatga gcaaagtgag atctgaggac acagcccttt attactgtgc aagaatggag      300
ttactctggt acttcgatgt ctggggcgca gggaccacgg tcaccgtctc ctca           354

<210> SEQ ID NO 40
<211> LENGTH: 339
<212> TYPE: DNA
<213> ORGANISM: Artificial Sequence
<220> FEATURE:
<223> OTHER INFORMATION: #50_VL

<400> SEQUENCE: 40
gacattgtga tgtcacagtc tccatcctcc ctagctgtgt cagttggaga gaaggttact       60
atgagctgca agtccagtca gagcctttta tatagtagca tcaaaagaa ctacttggcc      120 tggtaccagc agaaaccagg gcagtctcct aaactgctga tttactgggc atccactagg      180
gaatctgggg tccctgatcg cttcacaggc agtggatctg ggacagattt cactctcacc      240
atcagcagtg tgaaggctga agacctggca gtttattact gtcagcaata ttatagctat      300
ccgtggacgt tcggtggagg caccaagctg gaaatcaaa                             339

<210> SEQ ID NO 41
<211> LENGTH: 20
<212> TYPE: DNA
<213> ORGANISM: Artificial Sequence
<220> FEATURE:
<223> OTHER INFORMATION: PTK7 extracellular domain_forward primer
```

<400> SEQUENCE: 41
aaaagctcaa gttcacacca                                                              20

<210> SEQ ID NO 42
<211> LENGTH: 47
<212> TYPE: DNA
<213> ORGANISM: Artificial Sequence
<220> FEATURE:
<223> OTHER INFORMATION: PTK7 extracellular domain_reverse primer

<400> SEQUENCE: 42
gctctagatc aatgatgatg atgatgatgc tggatcatct tgtaggg                                47

<210> SEQ ID NO 43
<211> LENGTH: 98
<212> TYPE: PRT
<213> ORGANISM: Artificial Sequence
<220> FEATURE:
<223> OTHER INFORMATION: Ig loop(Ig2, Trp123-Ala220)

<400> SEQUENCE: 43

Trp Ile Glu Ala Gly Pro Val Val Leu Lys His Pro Ala Ser Glu Ala
1               5                   10                  15

Glu Ile Gln Pro Gln Thr Gln Val Thr Leu Arg Cys His Ile Asp Gly
                20                  25                  30

His Pro Arg Pro Thr Tyr Gln Trp Phe Arg Asp Gly Thr Pro Leu Ser
            35                  40                  45

Asp Gly Gln Ser Asn His Thr Val Ser Ser Lys Glu Arg Asn Leu Thr
        50                  55                  60

Leu Arg Pro Ala Gly Pro Glu His Ser Gly Leu Tyr Ser Cys Cys Ala
65                  70                  75                  80

His Ser Ala Phe Gly Gln Ala Cys Ser Ser Gln Asn Phe Thr Leu Ser
                85                  90                  95

Ile Ala

<210> SEQ ID NO 44
<211> LENGTH: 175
<212> TYPE: PRT
<213> ORGANISM: Artificial Sequence
<220> FEATURE:
<223> OTHER INFORMATION: Ig loop(Ig67, Arg529-Gln703)

<400> SEQUENCE: 44

Arg Glu Lys Pro Thr Ile Lys Trp Glu Arg Ala Asp Gly Ser Ser Leu
1               5                   10                  15

Pro Glu Trp Val Thr Asp Asn Ala Gly Thr Leu His Phe Ala Arg Val
                20                  25                  30

Thr Arg Asp Asp Ala Gly Asn Tyr Thr Cys Ile Ala Ser Asn Gly Pro
            35                  40                  45

Gln Gly Gln Ile Arg Ala His Val Gln Leu Thr Val Ala Val Phe Ile
        50                  55                  60

Thr Phe Lys Val Glu Pro Glu Arg Thr Thr Val Tyr Gln Gly His Thr
65                  70                  75                  80

Ala Leu Leu Gln Cys Glu Ala Gln Gly Asp Pro Lys Pro Leu Ile Gln
                85                  90                  95

Trp Lys Gly Lys Asp Arg Ile Leu Asp Pro Thr Lys Leu Gly Pro Arg
                100                 105                 110

Met His Ile Phe Gln Asn Gly Ser Leu Val Ile His Asp Val Ala Pro
            115                 120                 125

-continued

```
Glu Asp Ser Gly Arg Tyr Thr Cys Ile Ala Gly Asn Ser Cys Asn Ile
    130                 135                 140

Lys His Thr Glu Ala Pro Leu Tyr Val Val Asp Lys Pro Val Pro Glu
145                 150                 155                 160

Glu Ser Glu Gly Pro Gly Ser Pro Pro Pro Tyr Lys Met Ile Gln
                165                 170                 175
```

ANTIBODY SPECIFICALLY BINDING TO PTK7 AND USE THEREOF

This application is a national phase application of PCT Application No. PCT/KR2021/009208, filed on 16 Jul. 2021, which claims the benefit and priority to Korean Patent Application Nos. 10-2020-0088476, filed on 16 Jul. 2020 and 10-2021-0093285, filed on 16 Jul. 2021. The entire disclosures of the applications identified in this paragraph are incorporated herein by references.

TECHNICAL FIELD

The present invention relates to antibodies specifically binding to protein tyrosine kinase 7 (PTK7) and a use thereof. More particularly, the present invention relates to a PTK7 neutralizing antibodies specifically binding to PTK7 to inhibit PTK7 function, and a use thereof for inhibiting angiogenesis, cell proliferation, cell migration, and cell invasion.

BACKGROUND

A total of 58 receptor protein tyrosine kinases (RPTKs) are known in humans, and a typical RPTK consists of an extracellular domain to which ligands bind, a transmembrane domain, and an intracellular tyrosine kinase domain. When the ligands bind to the extracellular domain, RPTK dimerizes and a cytoplasmic domain is activated through phosphorylation to induce signaling.

However, defective RPTKs are a subgroup of RPTKs that become inactive due to a mutation in the tyrosine kinase domain that catalyzes phosphorylation. At least five members of defective RPTKs, which are ErbB3, PTK7, EphA10, EphB6, and RYK, have been reported in humans. Even though such defective RPTKs are not active, their physiological functions such as tumorigenesis have been proposed. For example, ErbB3 has been found to bind to other ErbB family members to induce oncogenic signaling processes, and an ErbB3 neutralizing human antibody (KTN3379) has been developed as an anti-cancer drug targeting ErbB3, which mediates drug resistance and is under clinical trials.

Human PTK7, first discovered and named by the inventors (Oncogene, 1993; 8:3403-10, J. Biochem., 1996; 119 (2): 235-9), is a defective RPTK. Specifically, a PTK7 polypeptide is composed of an ER signal peptide, an extracellular domain with seven immunoglobulin-like loops (hereinafter, referred to as Ig loops), a transmembrane domain, a juxtamembrane domain, a tyrosine kinase domain lacking catalytic activity, and a C-terminal tail region. PTK7 has been reported to be involved in axon guidance or heart formation during the development of *drosophila* and chickens, and has been reported to be involved in planar cell polarity (PCP) and Wnt signaling processes. In addition, PTK7 has been reported to bind to ROR2, one of RPTKs, during the development of *Xenopus*, a genus of frogs, to regulate planar cell polarity and neural crest migration.

In addition, increased PTK7 expression has been observed in various types of cancer, such as colorectal cancer, and PTK7 has been found to be involved in tumorigenesis and cancer metastasis. Specifically, the inventors have reported that PTK7 shed by ADAM17 in colorectal cancer cells is cleaved by γ-secretase to generate PTK7-CTF2, which transports to a nucleus and induces gene expression related to cell growth (J. Biol. Chem. 2012; 287:25001-9). In addition, the inventors have found that PTK7 plays an important role in angiogenesis (Biochem. Biophys. Res. Commun., 2008; 371:793-8). Through many studies as described above, PTK7 has been found to have mechanisms to promote tumorigenicity by activating RPTKs, such as KDR and FGFR1 (Biochim. Biophys. Acta, 2015; 1853:2251-60, FASEB J., 2019; 33:12960-71), and an association between PTK7 and development of various types of cancer have also been found. Therefore, PTK7 is attracting attention as a target gene for various types of cancer. However, since active sites of tyrosine kinase are modified in PTK7, the development of catalytic activity inhibitors is not easy, and a different approach is thus needed to inhibit PTK7 functions.

DISCLOSURE

Technical Problem

Under the above background, the inventors have studied to develop a neutralizing antibody that can be used for the treatment of various carcinomas by inhibiting PTK7 function. As a result, inhibitory effects on cancer cell growth, migration, invasion, and angiogenesis have been confirmed by the neutralizing antibodies specifically binding to an extracellular region of PTK7 to inhibit PTK7 activity, and the present invention has been thus completed.

Hence, an objective of the present invention is to provide anti-PTK7 antibodies or their functional fragments thereof, specifically binding to PTK7 and including heavy-chain variable regions and light-chain variable regions.

In addition, another objective of the present invention is to provide polynucleotides encoding the antibodies or their functional fragments.

In addition, a further objective of the present invention is to provide vectors containing the polynucleotides and cells transformed to the vectors.

In addition, a still another objective of the present invention is to provide a method of producing the antibodies or their functional fragments.

In addition, yet another objective of the present invention is to provide an angiogenesis inhibitor including the antibodies or their functional fragments as an active ingredient, and a pharmaceutical composition for preventing or treating an angiogenesis-related disease, the composition including the inhibitor as an active ingredient.

In addition, yet still another objective of the present invention is to provide an inhibitor for tumor cell growth, migration, or invasion, the inhibitor including the antibodies or their functional fragments as an active ingredient, and a pharmaceutical composition for preventing or treating cancer, the composition including the inhibitor as an active ingredient.

However, the technical problem to be achieved by the present invention is not limited to the above-mentioned problems, and other problems not mentioned will be clearly understood by those skilled in the art from the description below.

Technical Solution

To achieve the objectives of the present invention as described above, the present invention provides anti-PTK7 antibodies or functional fragments thereof, in which the antibodies specifically bind to PTK7 and include heavy-chain variable regions and light-chain variable regions.

The heavy-chain variable region includes CDR1-VH with an amino acid sequence of SEQ ID NO: 1, 7, 13, or 19, CDR2-VH with an amino acid sequence of SEQ ID NO: 2, 8, 14, or 20, and CDR3-VH with an amino acid sequence of SEQ ID NO: 3, 9, 15, or 21.

The light-chain variable region includes CDR1-VL with an amino acid sequence of SEQ ID NO: 4, 10, 16, or 22, CDR2-VL with an amino acid sequence of SEQ ID NO: 5, 11, 17, or 23, and CDR3-VL with an amino acid sequence of SEQ ID NO: 6, 12, 18, or 24.

As one embodiment of the present invention, the antibody or the functional fragment may include a heavy-chain variable region with an amino acid sequence of SEQ ID NO: 25 and a light-chain variable region with an amino acid sequence of SEQ ID NO: 26.

As another embodiment of the present invention, the antibody or the functional fragment may include a heavy-chain variable region with an amino acid sequence of SEQ ID NO: 27 and a light-chain variable region with an amino acid sequence of SEQ ID NO: 28.

As a further embodiment of the present invention, the antibody or the functional fragment may include a heavy-chain variable region with an amino acid sequence of SEQ ID NO: 29 and a light-chain variable region with an amino acid sequence of SEQ ID NO: 30.

As a further embodiment of the present invention, the antibody or the functional fragment may include a heavy-chain variable region with an amino acid sequence of SEQ ID NO: 31 and a light-chain variable region with an amino acid sequence of SEQ ID NO: 32.

As a further embodiment of the present invention, the antibodies or their functional fragments may specifically bind to an extracellular region of PTK7 protein.

As a further embodiment of the present invention, the antibody may be selected from the group consisting of IgG, IgA, IgM, IgE, and IgD, and the functional fragment may be selected from the group consisting of a diabody, Fab, F(ab'), F(ab')2, Fv, dsFv, and scFv.

As a further embodiment of the present invention, a PTK7 antigen-binding sites of the antibodies may be Ig loops.

As a further embodiment of the present invention, the Ig loop may be an Ig2 region (Trp123-Ala220) represented by SEQ ID NO: 43 or an Ig67 region (Arg529-Gln703) represented by SEQ ID NO: 44.

In addition, the present invention provides polynucleotides encoding the antibodies or their functional fragments.

In addition, the present invention provides vectors including the polynucleotides.

In addition, the present invention provides cells transformed to the vectors.

In addition, the present invention provides a method of producing an antibody specifically binding to PTK7 or a functional fragment thereof, the method including: producing a polypeptide containing a light-chain variable region and a heavy-chain variable region by culturing the cell; and collecting the polypeptide from the cell or a culture medium in which the cell is cultured.

In addition, the present invention provides an angiogenesis inhibitor including the anti-PTK7 antibody or the functional fragment as an active ingredient.

In addition, the present invention provides an inhibitor for tumor cell growth, migration, or invasion, the inhibitor including the anti-PTK7 antibody or the functional fragment as an active ingredient.

In addition, the present invention provides a pharmaceutical composition for preventing or treating a angiogenesis-related disease, the composition including the angiogenesis inhibitor as an active ingredient.

As one embodiment of the present invention, the angiogenesis-related disease may be selected from the group consisting of cancer, endometriosis, obesity, arthritis, arteriosclerosis, hemangioma, angiofibroma, vascular malformation, vascular adhesion, scleredema adultorum, diabetic retinopathy, macular degeneration, neovascular glaucoma, corneal diseases caused by angiogenesis, psoriasis, telangiectasia, pyogenic granuloma, seborrheic dermatitis, and Alzheimer's disease.

In addition, the present invention provides a pharmaceutical composition for preventing or treating cancer, the composition including the inhibitor for tumor cell growth, migration, or invasion as an active ingredient.

In addition, the present invention provides a method of preventing or treating an angiogenesis-related disease, the method including administering the pharmaceutical composition that includes the angiogenesis inhibitor as an active ingredient to a subject.

In addition, the present invention provides a preventive or therapeutic use of the pharmaceutical composition for an angiogenesis-related disease.

In addition, the present invention provides a method of preventing or treating cancer, the method including administering the pharmaceutical composition that includes the inhibitor for tumor cell growth, migration, or invasion as an active ingredient to a subject.

In addition, the present invention provides a preventive or therapeutic use of the pharmaceutical composition for cancer.

Advantageous Effects

Four types of human PTK7 neutralizing monoclonal antibodies, according to the present invention, have been confirmed to independently exhibit effective inhibitory effects on cancer cell growth, migration, and invasion in esophageal squamous cell carcinoma and triple-negative breast cancer and on angiogenesis. Therefore, the human PTK7 neutralizing monoclonal antibodies can be applied to various PTK7-positive carcinomas, and can be further developed as a targeted drug therapy for intractable cancer and angiogenic diseases to be used as a core global treatment drug for the same. In addition, the PTK7 neutralizing monoclonal antibodies can be converted into humanized antibodies, and can be thus used as essential materials in developing a new drug capable of being clinically used. Furthermore, the PTK7 neutralizing monoclonal antibodies can be used not only solely but also in combination with other drugs, such as existing anti-cancer drugs that are proven to be effective, to maximize anti-cancer treatment effects.

BRIEF DESCRIPTION OF DRAWINGS

FIG. 12 is a diagram showing amino acid sequence information for heavy-chain variable regions and light-chain variable regions of four types of PTK7 neutralizing monoclonal antibodies finally selected in the present invention;

BEST MODE

Figure 1:
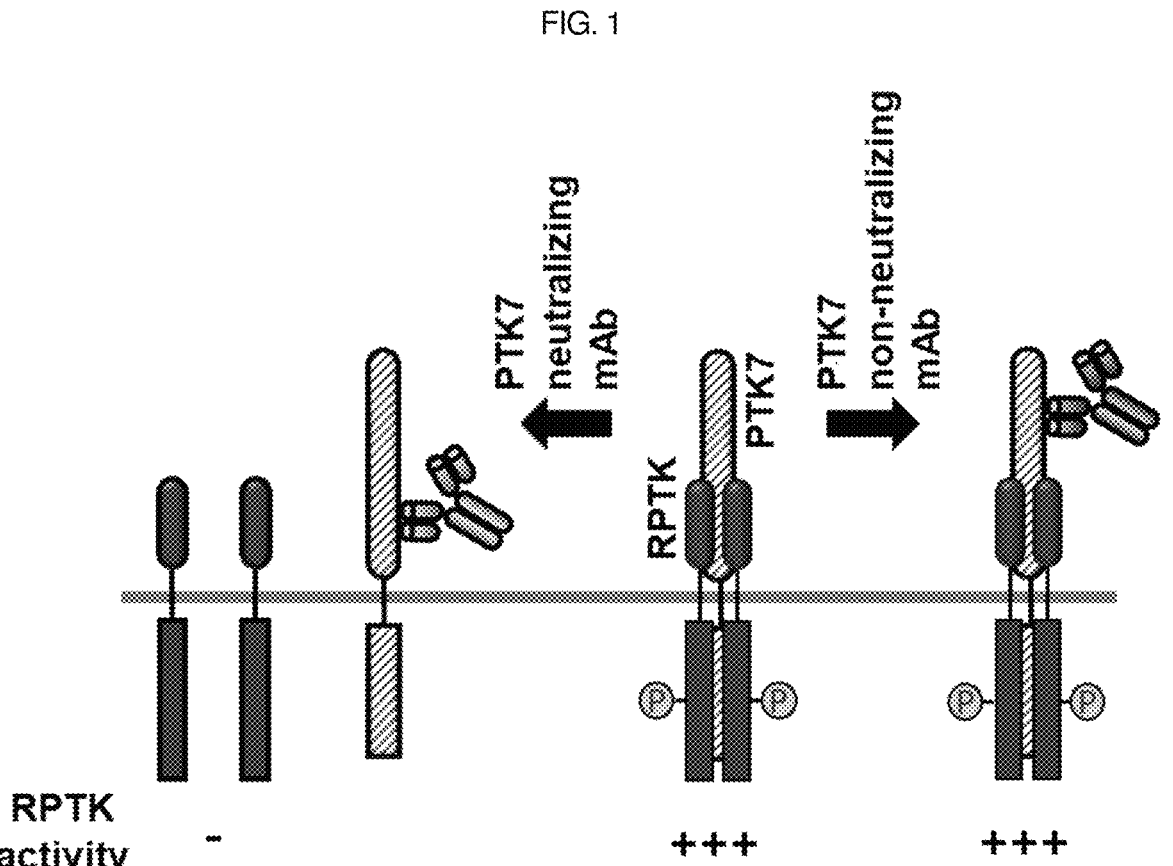
FIG. 1 is a schematic diagram illustrating modulation of RPTK activity by a PTK7 neutralizing monoclonal antibody (neutralizing mAb) and a non-neutralizing monoclonal antibody (non-neutralizing mAb)

The inventors have developed four types of human PTK7 neutralizing monoclonal antibodies to effectively inhibit a function of PTK7 in which development of catalytic activity inhibitors is not easy because an active site of tyrosine kinase is modified. In addition, the inventors have confirmed the inhibitory effects of the four types of human PTK7 neutralizing monoclonal antibodies on tumorigenesis, metastasis, and angiogenesis. As a result, the present invention has been completed.

Hence, the present invention provides anti-PTK7 antibodies or their functional fragments thereof in which the anti-PTK7 antibodies specifically bind to PTK7 and include heavy-chain variable regions and light-chain variable regions. The heavy-chain variable region includes CDR1-VH with an amino acid sequence of SEQ ID NO: 1, 7, 13 or 19, CDR2-VH with an amino acid sequence of SEQ ID NO: 2, 8, 14, or 20, and CDR3-VH with an amino acid sequence of SEQ ID NO: 3, 9, 15, or 21. In addition, the light-chain variable region includes CDR1-VL with an amino acid sequence of SEQ ID NO: 4, 10, 16, or 22, CDR2-VL with an amino acid sequence of SEQ ID NO: 5, 11, 17, or 23, and CDR3-VL with an amino acid sequence of SEQ ID NO: 6, 12, 18, or 24.

As used herein, the term "antibody" includes an immunoglobulin molecule immunologically having reactivity with a specific antigen, and includes both a polyclonal antibody and a monoclonal antibody. In addition, the term includes forms produced by genetic engineering, such as a chimeric antibody (for example, a humanized murine antibody), a heterologous antibody, and a bispecific antibody. In the present invention, the antibody is preferably the monoclonal antibody.

The terms 'antibody', 'anti-PTK7 antibody', and 'antibody specifically binding to PTK7' of the present invention are used in the broadest sense in the present invention, and specifically include a binding site specifically binding to PTK7.

The anti-PTK7 antibody or the functional fragment, according to the present invention, specifically binds to PTK7 and can be specifically attached to an extracellular domain of PTK7 with significantly high affinity.

Provided that PTK7 is well-known PTK7 in the art, the specific biological origin thereof is not particularly limited, and for example, may be derived from mammals including mice, humans, rats, chickens, dogs, or monkeys. Preferably, PTK7 is derived from humans.

Typically, an antibody has a heavy chain and a light chain, in which each of the heavy chain and the light chain includes a constant region and a variable region (the regions are also known as "domains"). The variable region of each of the heavy and light chains consists of one domain, and the variable regions thereof are called a heavy-chain variable region (VH) and a light-chain variable region (VL), respectively. In each of the heavy and light chains, the variable region and the constant region are aligned in parallel and connected by one covalent disulfide bond, and the heavy chains of the two molecules linked with the light chain are connected by two covalent disulfide bonds to form a whole antibody. The whole antibody specifically binds to an antigen through the heavy-chain variable region and the light-chain variable region. Since the whole antibody is composed of two heavy chains (HC) and two light chains (LC), one antibody molecule has bivalent monospecificity by which that the antibody binds to the same type of two antigens through the two variable regions.

The variable region including a site where the antibody binds to the antigen includes four framework regions and three variable regions called "complementarity-determining regions" (hereinafter, referred to as 'CDRs'). The CDR mainly serves to bind to an epitope of the antigen. Typically, the CDR in each chain is sequentially called CDR1, CDR2, and CDR3 starting from an N-terminal, and is also identified by the chain in which a particular CDR is located. However, not all CDR regions are required to be directly involved in antigen binding.

In the present invention, the antibody may be one selected from the group consisting of IgG, IgA, IgM, IgE, and IgD, and is preferably IgG. The IgG-type antibody includes all types of IgG$_1$, IgG$_2$, IgG$_3$, or IgG$_4$ subtypes.

The functional fragment of the present invention means a fragment of an antibody that retains antigen-specific binding ability of the whole antibody. The fragment has a PTK7 affinity of the parent antibody of at least 20%, 50%, 70%, or 80%, and preferably 90%, 95%, 96%, 97%, 98%, 99%, or 100% or more. Specifically, the fragment may be selected from the group consisting of a diabody, Fab, F(ab'), F(ab')2, Fv, dsFv, and scFv, and is not limited thereto.

In the present invention, the antibody or the fragment may contain a conservative amino acid substitution (referred to as a conservative variant of the antibody) that does not substantially modify the biological activity thereof.

The inventors produced the anti-PTK7 antibody in a specific example and confirmed anti-cancer effects according to PTK7 function inhibition of the anti-PTK7 antibody.

In one embodiment of the present invention, to produce a monoclonal antibody specifically binding to PTK7 protein, hybridoma cell lines for producing the antibody were constructed and selected. As a result, cell lines producing nine types of monoclonal antibodies with excellent binding ability to the extracellular domain as the antigen in a PTK7 protein structure were selected. In addition, nine types of antibodies were produced from each of the hybridoma cell lines (see Example 2).

In another example of the present invention, KYSE-30, an esophageal squamous cell carcinoma cell line, was treated with each of the nine types of the antibodies at two different concentrations, and the inhibitory effects on cell migration and adhesion were evaluated (see Example 3-1). In addition, to confirm whether each of the antibodies inhibits PTK7 activity at a molecular level, an HEK293 cell expressing FGFR1 was treated with each of the antibodies at two different concentrations, and the degree of inhibiting FGFR1 phosphorylation induced by acidic FGF was evaluated (see Example 3-2).

In a further example of the present invention, MDA-MB-231, a triple-negative breast cancer cell line, was treated with each of the nine types of antibodies at two different concentrations, and the inhibitory effects on cell migration and adhesion were evaluated. In addition, tyrosine phosphorylation and phosphorylation of Akt and Erk caused by antibody treatment were analyzed, and the inhibitory effects of each of the antibodies, according to the present invention, on cancer cell growth, cell adhesion, and oncogenic signaling processes were evaluated (see Example 4).

In still another embodiment of the present invention, five types of the antibodies exhibiting excellent anti-cancer effects based on the results of the above examples were selected, and then, whether each of the antibodies had an inhibitory effect on angiogenesis was examined. As a result, the inhibitory efficacy on VEGF-induced phosphorylation of a kinase insert domain receptor (KDR) and the inhibitory effect on migration of a cell expressing KDR were observed in each of the antibodies. Particularly, the four types of the antibodies exhibited excellent inhibitory activities (see Example 5).

From the evaluation results of the above examples, the final four antibodies with excellent anti-cancer effects and anti-angiogenic efficacy were selected. The anti-PTK7 antibodies or their functional fragments, according to the present invention, successfully blocked PTK7 function to effectively inhibit tumorigenesis, cancer metastasis and angiogenesis due to the expression or activation of PTK7 in various carcinomas. As a result, it is confirmed that their anti-cancer effects can be achieved.

In the present invention, preferably, the antibody or the functional fragment each independently includes: a heavy-chain variable region having an amino acid sequence of SEQ ID NO: 25 and a light-chain variable region having an amino acid sequence of SEQ ID NO: 26; a heavy-chain variable region having an amino acid sequence of SEQ ID NO: 27 and a light-chain variable region having an amino acid sequence of SEQ ID NO: 28; a heavy-chain variable region having an amino acid sequence of SEQ ID NO: 29 and a light-chain variable region having an amino acid sequence of SEQ ID NO: 30; or a heavy-chain variable region having an amino acid sequence of SEQ ID NO: 31 and a light-chain variable region having an amino acid sequence of SEQ ID NO: 32.

In addition, the present invention provides a polynucleotide encoding the antibody or the fragment.

As used herein, the term 'polynucleotide' may be described as an oligonucleotide or nucleic acid, and includes DNA molecules (for example, cDNA or genomic DNA), RNA molecules (for example, mRNA), analogs of the DNA or RNA generated using nucleotide analogs (for example, peptide nucleic acids and non-naturally occurring nucleotide analogs), and hybrids thereof. The polynucleotide may be single-stranded or double-stranded.

In the present invention, provided that the polynucleotide encodes the antibody or the fragment according to the present invention, a sequence of the polynucleotide is not particularly limited.

In the present invention, preferably, the antibody or the functional fragment each independently includes: a heavy-chain variable region having an amino acid sequence of SEQ ID NO: 33 and a light-chain variable region having an amino acid sequence of SEQ ID NO: 34; a heavy-chain variable region having an amino acid sequence of SEQ ID NO: 35 and a light-chain variable region having an amino acid sequence of SEQ ID NO: 36; a heavy-chain variable region having an amino acid sequence of SEQ ID NO: 37 and a light-chain variable region having an amino acid sequence of SEQ ID NO: 38; or a heavy-chain variable region having an amino acid sequence of SEQ ID NO: 39 and a light-chain variable region having an amino acid sequence of SEQ ID NO: 40.

The polynucleotide encoding the antibody or the fragment according to the present invention can be obtained by well-known methods in the art. For example, based on a DNA sequence partially or entirely coding the heavy chain and light chain of the antibody or the corresponding amino acid sequence, the polynucleotide can be synthesized using oligonucleotide synthesis techniques well-known in the art, such as polymerase chain reaction (PCR) and the like.

In the present invention, a PTK7 antigen-binding site of the antibody or the functional fragment may be an Ig loop of PTK7. More specifically, the Ig loop to which the PTK7 neutralizing antibody #43 of the present invention binds may be an Ig2 region represented by SEQ ID NO: 43 (Trp123-Ala220, Trp at position 123 or Ala at position 220), and the PTK7 neutralizing antibodies #32, #42, and #50 may be binds to an Ig67 region represented by SEQ ID NO: 44 (Arg529-Gln703, Arg at position 529 or Gln at position 703). The PTK7 antigen-binding site of the antibody or the functional fragment is not limited thereto.

In addition, the present invention provides a vector containing the polynucleotide.

As used herein, the term 'vector' is used for the purpose of the replication or expression of the polynucleotide of the present invention, for the recombinant production of the antibody or the fragment of the present invention. Generally, the vector includes one or more of a signal sequence, replication origin, one or more marker genes, an enhancer element, a promoter, and a transcription termination sequence. The vector of the present invention is preferably an expression vector, and more preferably a control sequence, for example, a vector containing the polynucleotide of the present invention operably linked to the promoter.

In addition, the present invention provides a cell transformed to the vector.

Provided that the cell can be used to express the polynucleotide encoding the antibody or the fragment, the cell of the present invention is not particularly limited. The cell (host cell) transformed to the expression vector, according to the present invention, may be a prokaryote (for example, *E. coli*), a eukaryote (for example, yeast or other fungi), a plant cell (for example, tobacco or a tomato plant cell), an animal cell (for example, a human cell, a monkey cell, a hamster cell, a rat cell, a mouse cell, an insect cell), or a hybridoma derived therefrom. Preferably, the cell is derived from mammals including humans.

As used herein, the term 'transformation' means a modification of the genotype of the host cell due to the introduction of a foreign polynucleotide, and means that the foreign polynucleotide is introduced into the host cell regardless of the method used for the transformation. While the foreign polynucleotide introduced into the host cell may either remain integrated into the genome of the host cell or may remain unintegrated, both of which are encompassed by the present invention.

A recombinant expression vector capable of expressing the anti-PTK7 antibody or the functional fragment, according to the present invention, can be introduced into the cell for producing an antibody or a fragment thereof to be transformed by methods known in the art, such as transient transfection, microinjection, transduction, cell fusion, calcium phosphate precipitation, liposome-mediated transfection, DEAE dextran-mediated transfection, polybrene-mediated transfection, electroporation, gene gun, and known methods for introducing nucleic acids into cells. The transformation method is not limited thereto.

In addition, the present invention provides a method of producing an antibody specifically binding to PTK7 or a functional fragment thereof including: producing a polypeptide containing a light-chain variable region and a heavy-chain variable region by culturing the cell; and collecting the polypeptide from the cell or a culture medium in which the cell is cultured.

In the cell culture, medium compositions and culture conditions may vary according to types of cell, which can be appropriately selected and adjusted by those skilled in the art.

A molecule of the antibody may be accumulated in the cytoplasm of cells, secreted from cells, or targeted to the periplasm or extracellular medium (supernatant) using a proper signal sequence. In addition, the produced antibody molecule is preferably refolded using a method well-known to those skilled in the art to have a functional conformation. The collection of the polypeptide may vary according to characteristics of the produced polypeptide and characteristics of the cell, which can be appropriately selected and adjusted by those skilled in the art.

In addition, the present invention provides a method of specifically detecting PTK7 including: bringing the antibody or the fragment into contact with a sample; and detecting the antibody or the fragment.

Those skilled in the art can appropriately select a known method of detecting protein using an antibody and can produce a suitable sample for the selected method. In addition, the sample may be a cell obtained by a biopsy taken from a subject to be diagnosed with cancer or cancer metastasis, tissue, blood, whole blood, serum, blood plasma, saliva, cerebrospinal fluid, or the like. The method of detecting protein using the antibody is not limited thereto, and examples thereof include western blot, immunoblot, dot blot, immunohistochemistry, enzyme-linked immunosorbent assay (ELISA), radioimmunoassay, competitive binding assays, immunoprecipitation, and the like.

The antibody or the fragment may be generally labeled with a detectable moiety for 'detection' thereof. For example, the antibody or the fragment may be labeled with a radioactive isotope or a fluorescent label, and various enzyme-substrate labels are available. Examples of the enzymatic labels include luciferases, such as firefly luciferase and bacterial luciferase, luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (for example, glucose oxidase, galactose oxidase, and glucose-6-phosphate dehydrogenase), heterocyclic oxidases (for example, uricase and xanthine oxidase), lactose peroxidase, microperoxidase, and the like. Conjugation of an enzyme and the antibody may be performed directly or indirectly using known techniques. For example, the antibody may be conjugated to biotin, and any labels belonging to the three broad categories mentioned above may be conjugated to avidin or vice versa. Biotin selectively binds to avidin and the label thereof can be thus conjugated to the antibody in such indirect way.

As another aspect of the present invention, the present invention provides an angiogenesis inhibitor including the anti-PTK7 antibody or the functional fragment as an active ingredient.

In addition, the present invention provides an inhibitor for tumor cell growth, migration, or invasion, the inhibitor including the anti-PTK7 antibody or the functional fragment as an active ingredient.

In addition, the present invention provides a pharmaceutical composition for preventing or treating angiogenesis-related diseases, the composition including the angiogenesis inhibitor as an active ingredient.

In the present invention, the "angiogenesis-related disease" is a disease that can be induced by continuous abnormal or excessive angiogenesis, and may be specifically selected from the group consisting of cancer, endometriosis, obesity, arthritis, arteriosclerosis, hemangioma, angiofibroma, vascular malformation, vascular adhesion, scleredema adultorum, diabetic retinopathy, macular degeneration, neovascular glaucoma, corneal diseases caused by angiogenesis, psoriasis, telangiectasia, pyogenic granuloma, seborrheic dermatitis, and Alzheimer's disease. The disease is not limited thereto.

In addition, the present invention provides a pharmaceutical composition for preventing or treating cancer, the composition including the inhibitor for tumor cell growth, migration, or invasion as an active ingredient.

In the present invention, the expression or activity of PTK7 is preferably increased in the cancer. Specifically, the cancer may be any one selected from the group consisting of bladder cancer, bone cancer, blood cancer, breast cancer, melanoma, thyroid cancer, parathyroid cancer, bone marrow cancer, rectal cancer, throat cancer, larynx cancer, lung cancer, esophageal cancer, pancreatic cancer, stomach cancer, tongue cancer, skin cancer, brain tumor, uterine cancer, head or neck cancer, gallbladder cancer, oral cancer, colon cancer, perianal cancer, central nervous system tumor, liver cancer, and colorectal cancer, and is not limited thereto.

The pharmaceutical composition according to the present invention includes an angiogenesis inhibitor including an anti-PTK7 antibody or a functional fragment or an inhibitor for tumor cell growth, migration, or invasion as an active ingredient, and may further include a pharmaceutically acceptable carrier. The pharmaceutically acceptable carrier, which is typically used during formulation, includes a saline solution, sterile water, a Ringer's solution, cyclodextrin, a dextrose solution, a maltodextrin solution, glycerol, ethanol, liposome, and the like, and not limited thereto. The carrier may further include other commonly known additives, such as antioxidants, buffer solutions, and the like, as needed. In addition, diluents, dispersants, surfactants, binders, lubricants, and the like may be additionally added to be formulated into injectable formulations, such as aqueous solutions, suspensions, emulsions, and the like, pills, capsules, granules, or tablets. Regarding the suitable pharmaceutically acceptable carrier and formulation, each component is preferably formulated using methods disclosed in Remington's literature. In the present invention, formulation of the pharmaceutical composition is not particularly limited and the pharmaceutical composition may be formulated as injections, inhalants, skin external preparations, and the like.

The pharmaceutical composition of the present invention may be administered orally or parenterally (for example, intravenously, subcutaneously, intraperitoneally, or topically applied) depending on the desired method. A dosage of the pharmaceutical composition may vary according to condition, body weight, and disease of a patient, severity of the disease, drug types, administration routes, and administration times, and may be appropriately selected by those skilled in the art.

The pharmaceutical composition of the present invention is administered in a pharmaceutically effective amount. In the present invention, "pharmaceutically effective amount" means an amount sufficient to treat or diagnose a disease at a reasonable benefit-risk ratio applicable to medical treatment or diagnosis. The effective dose level may be determined according to types of disease, severity, drug activity, sensitivity to drug, administration time, administration route and rate of release, duration of treatment, factors including concurrent medications, and other factors well-known in the medical field. The pharmaceutical composition according to the present invention may be administered as a single therapeutic agent or in combination with other therapeutic agents, may be administered sequentially or simultaneously with conventional therapeutic agents, and may be administered once or multiple times. Considering all of the above factors, administering an amount capable of obtaining the maximum effects with the minimum amount without side effects is critical, which can be easily determined by those skilled in the art.

Specifically, the effective amount of the pharmaceutical composition of the present invention may vary depending on age, sex, condition, and body weight of a patient, an absorption rate of the active ingredient in the body, an inactivation rate, an excretion rate, a type of disease, and a drug used in combination. Typically, the pharmaceutical composition may be administered in an effective amount in a range of 0.001 mg to 150 mg per 1 kg of body weight, and preferably, in the range of 0.01 mg to 100 mg daily or every other day, or one time to three times a day. However, the effective amount may increase or decrease depending on administration routes, severity of obesity, gender, weight, age, and the like, so the dosage is not limited to the scope of the present invention in any way.

As a further aspect of the present invention, the present invention provides a method of preventing or treating angiogenesis-related diseases, the method including administering the pharmaceutical composition to a subject.

As still another aspect of the present invention, the present invention provides a method of preventing or treating cancer, the method including administering the pharmaceutical composition to a subject.

In the present invention, "subject" means a subject in need of treatment for a disease, and more specifically, means mammals, such as humans or non-human primates, mice, rats, dogs, cats, horses, cows, and the like.

In addition, the present invention provides a preventive or therapeutic use of the pharmaceutical composition for an angiogenesis-related disease.

In addition, the present invention provides a preventive or therapeutic use of the pharmaceutical composition for cancer.

Hereinafter, preferred embodiments of the present invention will be presented to aid understanding of the present invention. However, the following examples are only provided to more easily understand the present invention, and the content of the present invention is not limited by the following examples.

EXAMPLE

Example 1. Experiment Material and Experiment Method 1-1. Cell Culture

Human fetal kidney HEK293 cells, esophageal squamous cell carcinoma KYSE-30 cells, and triple-negative breast cancer MDA-MB-231 cells used in the examples of the present invention were cultured at a temperature of 37° C. in the presence of 5% of CO2 and 95% of air using Dulbecco's Modified Eagle Medium (DMEM) containing 10% of FBS, 100 unit/ml of penicillin, and 100 μg/ml of streptomycin.

1-2. Preparation of His-Tagged Human sPTK7 Expression Plasmid

First, a 4.2-kb EcoRI fragment was obtained from human PTK7 full-length cDNA (J Biochem (Tokyo) 119:235-239), and subcloned into an EcoRI site of a pcDNA3 vector (purchased from Invitrogen) to construct pcDNA3-hPTK7, a human PTK7 expression vector. A 640-bp cDNA fragment encoding a C-terminal portion of an extracellular domain of human PTK7 protein was amplified through a polymerase chain reaction (PCR) to include a His-tag coding sequence and a translation termination codon. A primer pair used for PCR was 5'-AAAAGCTCAAGTTCACACCA-3' (SEQ ID NO: 41) (nucleotide position 1646-1665 of GenBank U40271) and 5'-GCTCTAGATCAATGATGATGATGAT-GATGCTGGATCATCTTGTAGGG-3' (SEQ ID NO: 42) [nucleotide position 2239-2256 of GenBank U40271, a His-tag coding sequence (the underlined portion in the above sequence), a stop codon, and an XbaI site (the italicized portion in the above sequence)]. The resulting PCR product was digested with XhoI and XbaI to isolate a 0.45-kb fragment. pcDNA3-hPTK7 was also digested with XhoI (the nucleotide position 1829 of GenBank U40271) and XbaI (a multi-cloning site of pcDNA3) to remove a 1.6-kb fragment. As a result of ligating XhoI and XbaI-cleaved cDNA3-hPTK7 vector with the XhoI and XbaI-cleaved 0.45-kb fragment, a pcDNA3-hPTK7-Ext-His plasmid, a human sPTK7 expression vector, was obtained. Through bidirectional sequencing, the resulting plasmid was confirmed to have no PCR error.

Example 2. Production of PTK7 Monoclonal Antibodies 2-1. Construction and Selection of PTK7 Monoclonal Antibody-Producing Hybridoma Cell Lines To produce a monoclonal antibody that specifically binds to PTK7 protein, the inventors first attempted to construct and select hybridoma cell lines for producing the antibody.

Figure 2A:
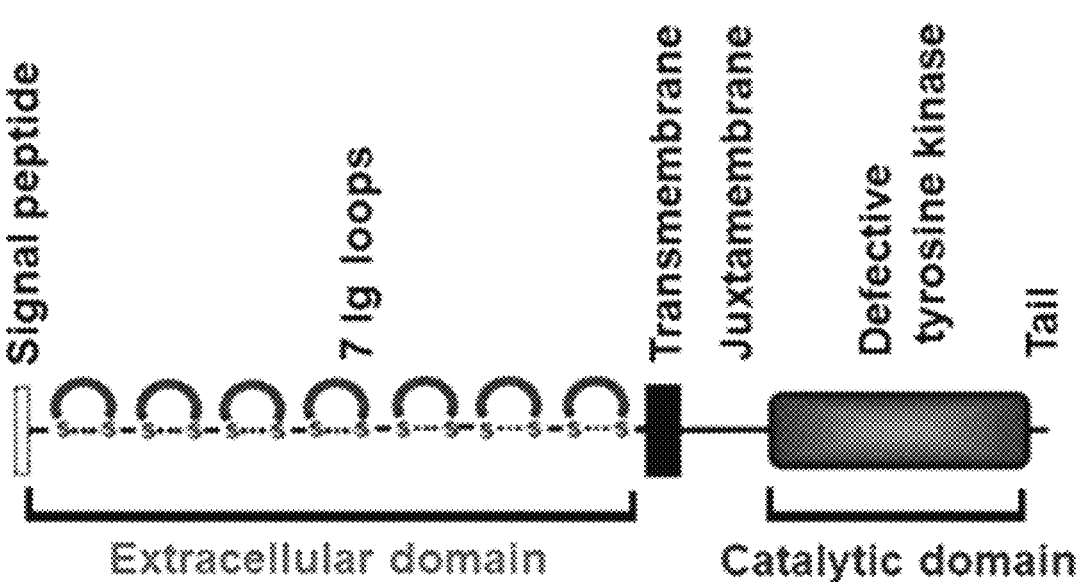
FIG. 2A is a diagram illustrating a PTK7 protein structure.
Figure 2B:
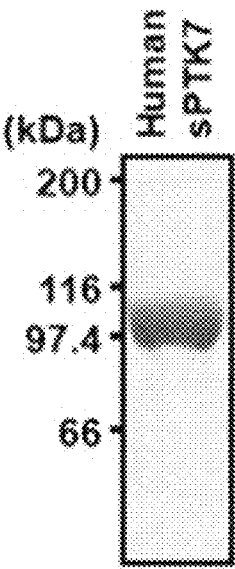
FIG. 2B is a diagram illustrating a purification result of human sPTK7 protein by culturing a HEK293 cell expressing soluble PTK7 (sPTK7) corresponding to an extracellular domain of PTK7, precipitating protein in a culture medium with ammonium sulfate, and then performing chromatography.

To this end, pcDNA3-hPTK7-Ext-His, the sPTK7 expression vector prepared by the method of Example 1-2, expressing an extracellular domain (soluble PTK7; sPTK7) in a PTK7 protein structure as illustrated in FIG. 2A was transfected into HEK293 cells by a calcium phosphate method, and then treated with 1.2 mg/ml of G418 to select G418-resistant cell clones. Cell clones stably expressing human sPTK7 with His tag were reselected from the selected cell clones by western blotting using an anti-Penta-His monoclonal antibody (Qiagen, Hilden, Germany). Thereafter, the cell clones stably expressing human sPTK7 were cultured in a serum-free medium for 7 days to obtain a culture medium, and phenylmethanesulfonyl fluoride (PMSF) and ethylene diamine tetraacetic acid (EDTA) were each independently added thereto at a concentration of 1 mM. The culture medium was saturated up to 70% with the addition of ammonium sulfate to precipitate proteins, and then the precipitates were dissolved with phosphate-buffered saline (50 mM $NaH_2PO_4$, pH7.4, 150 mM NaCl) containing 1 mM phenylmethylsulfonyl fluoride and 1 mM ethylene diamine tetraacetic acid and dialyzed with phosphate-buffered saline. The dialyzed samples were loaded onto $Ni^{2+}$-NTA agarose (purchased from Qiagen), eluted with imidazole, and then re-dialyzed with phosphate-buffered saline to obtain purified human sPTK7. The purification results are shown in FIG. 2B.

Next, mouse anti-PTK7 hybridoma cell lines were prepared using the purified human sPTK7 as an antigen, and a culture medium of each of the cell lines was collected to analyze the reactivity with PTK7 by performing ELISA. As a result of the analysis, the cell lines producing nine types of monoclonal antibodies (PTK7 mAb #1, 6, 32, 39, 42, 43, 46, 49, and 50) with excellent binding ability to PTK7 were selected.

2-2. Purification of Nine Types of PTK7 Antibodies from Selected Hybridoma Cell Lines To purify PTK7 antibodies from each of the cell lines selected in Example 2-1, hybridoma cell lines secreting nine types of the human PTK7 monoclonal antibodies with excellent PTK7 binding ability were cultured. Each of the hybridoma cell lines was cultured in a serum-free medium to obtain a culture medium, and phenylmethanesulfonyl fluoride and ethylene diamine tetraacetic acid were each independently added thereto at a concentration of 1 mM. The culture medium was saturated up to 50% with the addition of ammonium sulfate to precipitate proteins, and then the precipitates were dissolved with a 0.1 M Tris-HCl (pH8.0) solution containing 1 mM phenylmethylsulfonyl fluoride and 1 mM ethylene diamine tetraacetic acid. The dissolved samples were loaded onto a protein A/G agarose column and washed with a 0.1 M Tris-HCl (pH8.0) solution, followed by a 10 mM Tris-HCl (pH8.0) solution, and then the antibodies were eluted with 0.1 M Glycine-HCl (pH 2.8). The eluted antibodies were neutralized with the addition of 1 M Tris-HCl (pH 8.0) at a volume that is ¹⁄₁₀ of the eluted volume, and then dialyzed with phosphate-buffered saline. It was confirmed that final amount of the monoclonal antibodies purified by culturing the hybridoma cell lines, according to the above method, was in a range of 0.64 mg to 2.5 mg, based on 100 ml of the culture medium.

Example 3. Analysis of Anti-Cancer Effects of PTK7 Monoclonal Antibodies in Esophageal Squamous Cell Carcinoma Cells As PTK7 is highly expressed in various cancers and is known to be involved in tumorigenesis and metastasis, PTK7 has attracted attention as an anti-cancer target molecule. Hence, the inventors first attempted to verify the effects of the PTK7 monoclonal antibodies produced in Example 2 on esophageal squamous cell carcinoma.

3-1. Analysis of Anti-Cancer Effects of PTK7 Monoclonal Antibodies

The inventors have confirmed the correlation between esophageal squamous cell carcinoma and PTK7 through previous studies. Specifically, knocking-down PTK7 in TE-10 and TE-11, which are esophageal squamous cell carcinoma cells, inhibited cell growth, and reduced cell migration and invasion (Cancer Sci. 2013; 104:1120-6). In addition, oncogenic phenotypes according to PTK7 expression were analyzed in KYSE-30, an esophageal squamous cell carcinoma cell line in which EGFR, an oncogene, was overexpressed and p53, a tumor suppressor gene, was mutated. Knocking-down PTK7 in the cells decreased the cell growth and adhesion, and overexpressing PTK7 increased the cell growth and adhesion. Furthermore, it was confirmed that serum-induced tyrosine phosphorylation of cytoplasmic proteins and phosphorylation of Erk, Akt, and FAK were reduced upon the PTK7-knockdown in the cells.

Figure 3:
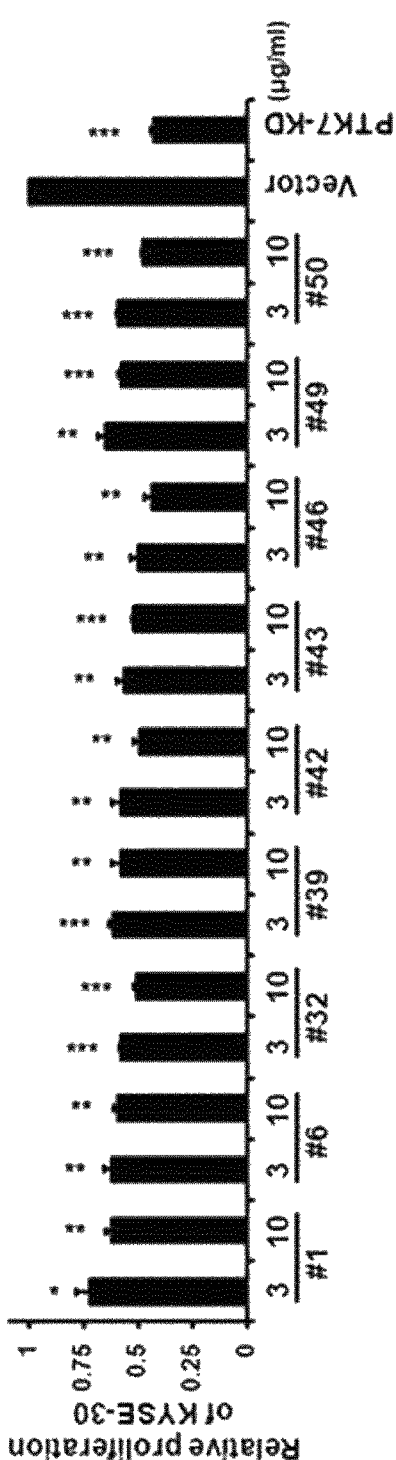
FIG. 3 is a graph showing the inhibitory effect of serum-induced cell growth by each of nine types of PTK7 monoclonal antibodies at a concentration of 3 μg/ml or 10 μg/ml in KYSE-30, an esophageal squamous cell carcinoma cell line (*P<0.05, P<0.01, *P<0.001 vs. Vector. N=3)

Hence, based on the results of previous studies, the inventors analyzed whether the above-described anti-cancer effects were exhibited when KYSE-30, the esophageal squamous cell carcinoma cell line, was treated with the nine types of the PTK7 monoclonal antibodies. To this end, the KYSE-30 cells were first treated with the nine types of the PTK7 monoclonal antibodies produced in Example 2 at a concentration of 3 µg/ml or 10 µg/ml, and the degree of cell growth induced by 10% of fetal bovine serum was analyzed using an MTT test method. As a result, as shown in FIG. 3, when being treated with each of the antibodies at a concentration of 3 µg/ml, it was confirmed that the inhibitory effect on the cell growth was exhibited in the order of 46>43>32>42>50>39>6>49>1. In addition, when being treated with each of the antibodies at a concentration of 10 µg/ml, it was confirmed that the inhibitory effect on the cell growth was exhibited in the order of 46>50>42>32>43>39>49>6>1.

Figure 4:
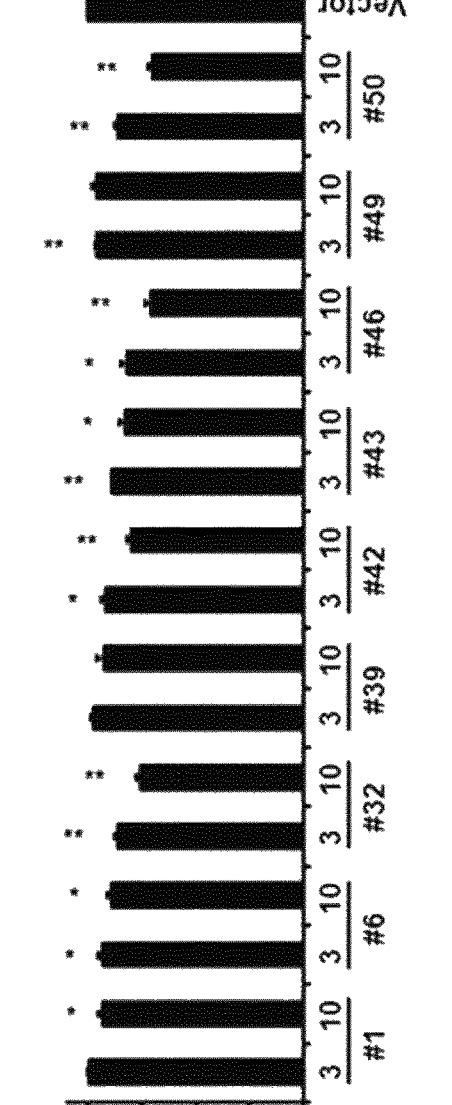
FIG. 4 is a graph showing the inhibitory effect of cell adhesion in a collagen-coated culture vessel by each of nine types of PTK7 monoclonal antibodies at a concentration of 3 μg/ml or 10 μg/ml in KYSE-30 cell line (*P<0.05, P<0.01, *P<0.001 vs. Vector. N=3)

In addition, the KYSE-30 cell was treated with the nine types of the PTK7 monoclonal antibodies at a concentration of 3 µg/ml or 10 µg/ml, and then the degree of cell adhesion was analyzed in the presence of 1% of fetal bovine serum in a 96-well plate coated with 1 µg/ml of rat tail collagen. As a result, as shown in FIG. 4, when being treated with each of the antibodies at a concentration of 3 µg/ml, it was confirmed that the inhibitory effect on the cell adhesion was exhibited in the order of 46>32>50>43>42>6>49>39>1. In addition, when being treated with each of the antibodies at a concentration of 10 µg/ml, it was confirmed that adhesion inhibition effect was exhibited in the order of 50>46>32>42>43>6>39>1>49. When considering the above results together, it was seen that the PTK7 monoclonal antibodies 32, 42, 43, 46, and 50 had excellent neutralizing abilities in terms of inhibiting the KYSE-30 cell growth and adhesion.

Figure 5:
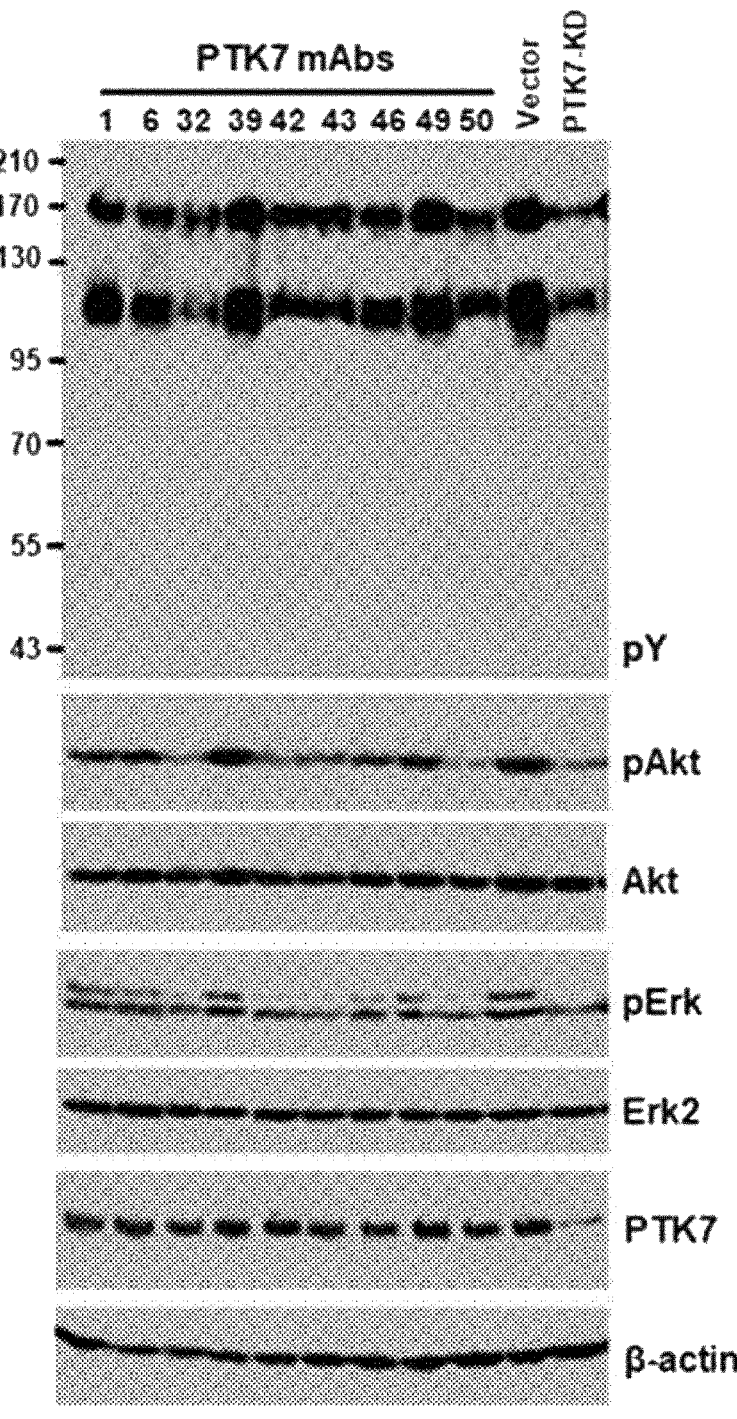
FIG. 5 is a diagram showing the inhibitory effect of serum-induced tyrosine phosphorylation (pY) of cytoplasmic proteins and phosphorylation of Akt and Erk (pAkt and pErk) by each of nine types of PTK7 monoclonal antibodies at a concentration of 3 μg/ml in KYSE-30 cell line.

In addition, the serum-induced tyrosine phosphorylation of cellular proteins and phosphorylation of Akt and Erk were analyzed after treating the KYSE-30 cells with the nine types of PTK7 monoclonal antibodies at a concentration of 3 µg/ml. As a result, as shown in FIG. 5, it was confirmed that the antibodies 32, 42, 43, 46, and 50 had excellent neutralizing abilities.

3-2. Analysis of Inhibitory Effects of PTK7 Monoclonal Antibodies on FGFR1 Phosphorylation Through previous studies, the inventors also confirmed that PTK7 bound to and activated FGFR1 in the esophageal squamous cell carcinoma cells to promote oncogenic phenotypes and oncogenic signaling (FASEB J., 2019; 33:12960-71). Hence, the inventors attempted to confirm whether PTK7 monoclonal antibodies according to the present invention exhibited inhibitory effects on FGFR1 phosphorylation.

Figure 6:
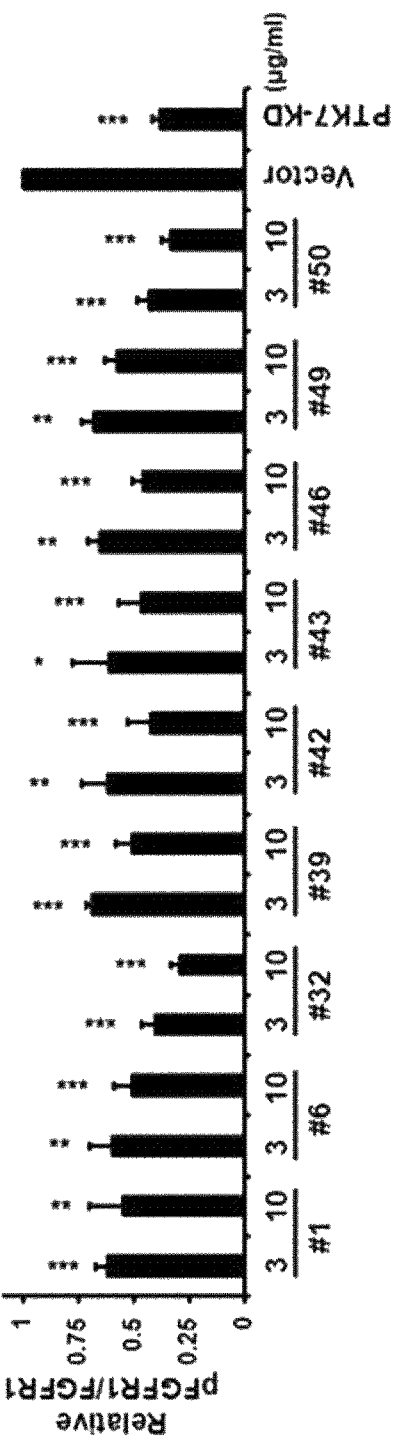
FIG. 6 is a graph showing the inhibitory effect of acidic FGF-induced FGFR1 phosphorylation by each of nine types of PTK7 monoclonal antibodies at a concentration of 3 μg/ml or 10 μg/ml in HEK293 cells expressing FGFR1 (*P<0.05, P<0.01, *P<0.001 vs. Vector. N=5)

To this end, HEK293 cells expressing FGFR1 were treated with the nine types of the PTK7 monoclonal antibodies at a concentration of 3 µg/ml or 10 µg/ml, and then the degree of inhibiting FGFR1 phosphorylation induced by 10 ng/ml of acidic FGF was analyzed. As a result, as shown in FIG. 6, when being treated with each of the antibodies at a concentration of 3 µg/ml, the degree of inhibiting the FGFR1 phosphorylation in the HEK293 cells was exhibited in the order of 32>50>6>43>42>1>46>49>39. In addition, when being treated with each of the antibodies at a concentration of 10 µg/ml, the degree of inhibiting the FGFR1 phosphorylation in the HEK293 cells was exhibited in the order of 32>50>42>46>43>39>6>1>49. When analyzing FGFR1 phosphorylation in the HEK293 cells overexpressing FGFR1, the inhibitory effect due to the PTK7 neutralizing antibodies 32, 42, 43, and 50 at low concentrations was found to be similar to the effect from analysis results of the oncogenic phenotypes and oncogenic signaling in the KYSE-30 cells. However, in the case of the PTK7 neutralizing antibody 46, the efficacy was observed to be low. Nevertheless, in the case of the inhibitory effect by the PTK7 antibodies at a high concentration, it was confirmed that the PTK7 neutralizing antibodies 32, 42, 43, 46, and 50 exhibited excellent neutralizing ability, which was consistent with the other analysis results.

Example 4. Analysis of Anti-Cancer Effects of PTK7 Monoclonal Antibodies in Triple-Negative Breast Cancer Cells Through previous studies, the inventors analyzed a change in oncogenic phenotypes according to PTK7 expression in triple-negative breast cancer cell lines. Specifically, PTK7 expression level was analyzed in each of estrogen receptor-positive (ER+) breast cancer cell lines and basal-A, basal-B, and luminal types of triple-negative breast cancer cell lines. As a result, the PTK7 expression was observed in all of the cell lines. However, the PTK7 expression was high in the triple-negative breast cancer cell lines compared to the ER+ breast cancer cell lines. Based on the results, a change in oncogenic phenotypes and signaling processes according to the PTK7 expression in the triple-negative breast cancer cells was analyzed on an MDA-MB-231 cell line, which has been widely used in mouse xenotransplantation studies, among three-negative breast cancer cells. When knocking-down PTK7 in the cells, fetal bovine serum-induced cell growth, cell adhesion in a culture dish coated with collagen or fibronectin, cell migration, and cell invasion were reduced. In addition, PTK7-knockdown inhibited cell growth was inhibited and phosphorylation of FAK, Akt, and ERK, which play an important role in oncogenic signaling, was reduced in MDA-MB-436 and MDA-MB-453 cells, other triple-negative breast cancer cells. Through the results, it was seen that the PTK7-knockdown in the triple-negative breast cancer cells commonly inhibited the oncogenic phenotypes and oncogenic signaling processes.

Figure 7:
FIG. 7 is a graph showing the inhibitory effect of serum-induced cell growth by each of nine types of PTK7 monoclonal antibodies at a concentration of 3 μg/ml or 10 μg/ml in MDA-MB-231, a triple-negative breast cancer cell line (*P<0.05, P<0.01, *P<0.001 vs. Vector. N=3)

Hence, based on the results of the above studies, it was analyzed whether the anti-cancer effects as described above were observed when MDA-MB-231, the triple-negative breast cancer cell line, was treated with the nine types of PTK7 monoclonal antibodies according to the present invention. To this end, the MDA-MB-231 cell was first treated with the nine types of the PTK7 monoclonal antibodies produced in Example 2 at a concentration of 3 µg/ml or 10 µg/ml in the same manner as in Example 3-1 to analyze the degree of cell growth induced by fetal bovine serum. As a result, as shown in FIG. 7, when being treated with each of the antibodies at a concentration of 3 µg/ml, it was confirmed that the inhibitory effect on the cell growth was exhibited in the order of 42>50>32>43>6>46>39>1>49. In addition, when being treated with each of the antibodies at a concentration of 10 µg/ml, it was confirmed that the inhibitory effect on the cell growth was exhibited in the order of 42>50>32>46>43>6>39>1>49.

Figure 8:
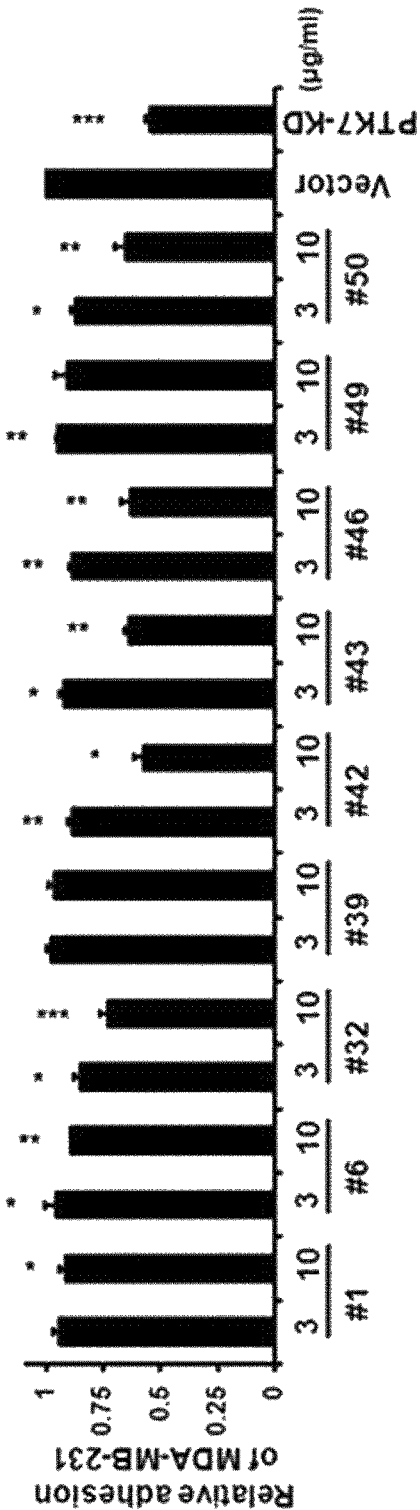
FIG. 8 is a graph showing the inhibitory effect of cell adhesion in a collagen-coated culture vessel by each of nine types of PTK7 monoclonal antibodies at a concentration of 3 μg/ml or 10 μg/ml in MDA-MB-231 cell line (*P<0.05, P<0.01, *P<0.001 vs. Vector. N=3)

In addition, in the same manner as in Example 3-1, the MDA-MB-231 cells were treated with the nine types of the PTK7 monoclonal antibodies at a concentration of 3 µg/ml or 10 µg/ml to analyze the degree of cell adhesion induced by fetal bovine serum. As a result, as shown in FIG. 8, when being treated with each of the antibodies at a concentration of 3 µg/ml, the inhibitory effect on the cell adhesion was exhibited in the order of 32>50>42>46>43>1>49>6>39. In addition, when being treated with each of the antibodies at a concentration of 10 µg/ml, the inhibitory effect on the cell adhesion was exhibited in the order of 42>46>43>50>32>6>49>1>39.

Figure 9:
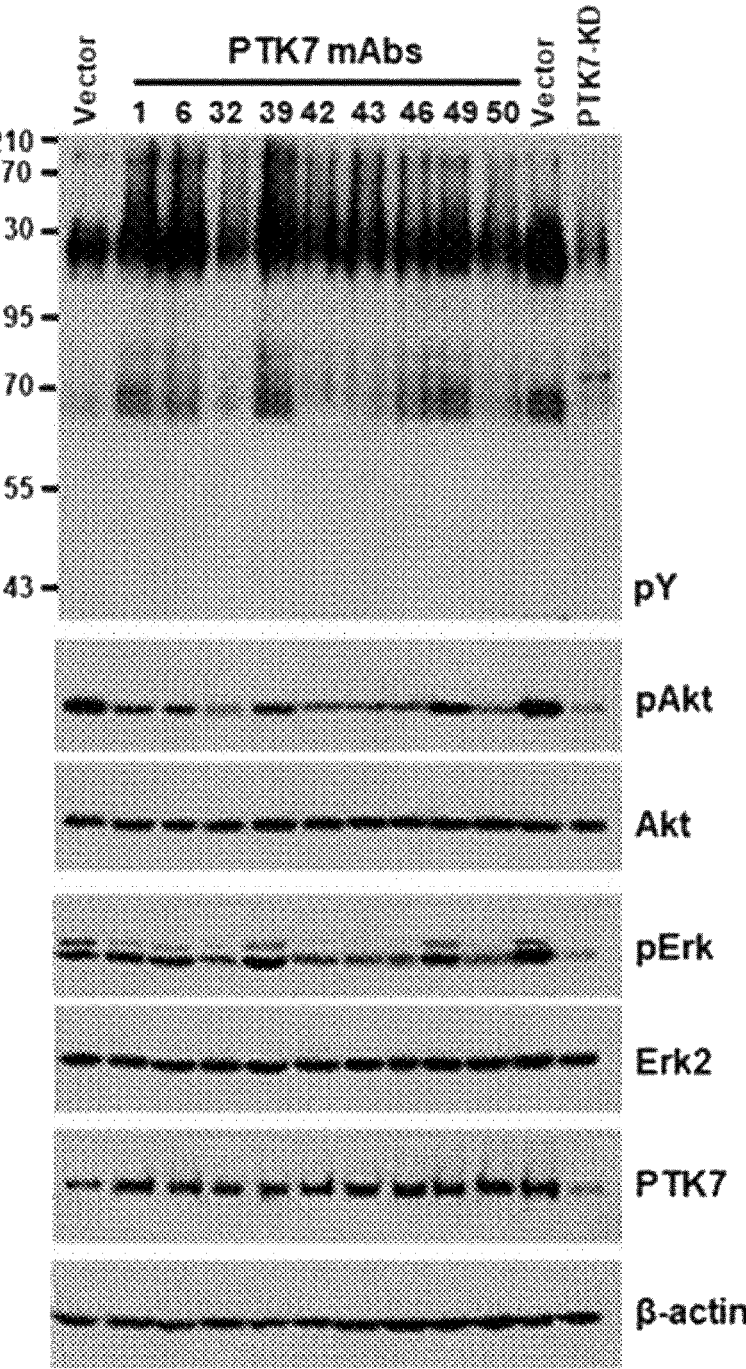
FIG. 9 is a diagram showing the inhibitory effect of serum-induced tyrosine phosphorylation (pY) of cytoplasmic proteins and phosphorylation of Akt and Erk (pAkt and pErk) by each of nine types of PTK7 monoclonal antibodies at a concentration of 3 μg/ml in MDA-MB-231 cell line.

In addition, when analyzing tyrosine phosphorylation of cellular proteins and phosphorylation of Akt and Erk after treating an MDA-MB-231 cell with the nine types of PTK7 monoclonal antibodies at a concentration of 3 µg/ml, it was confirmed that the neutralizing ability due to the PTK7 monoclonal antibodies 32, 42, 43, 46, and 50 was excellent, as shown in FIG. 9.

When considering the above results together, it was seen that the antibodies 32, 42, 43, 46, and 50 were excellent in terms of inhibiting the cell growth, cell adhesion, and oncogenic signaling processes in the triple-negative breast cancer MDA-MB-231 cells, which is consistent with the results in the esophageal squamous cell carcinoma cells. Thus, the antibodies 32, 42, 43, 46, and 50 among the nine types of the PTK7 monoclonal antibodies were selected as PTK7 neutralizing monoclonal antibodies with excellent anti-cancer effects.

Example 5. Analysis of Inhibition of Angiogenic Signaling by PTK7 Monoclonal Antibodies The inventors found that PTK7 expression increases tube formation of vascular endothelial cells and in vivo angiogenesis. Specifically, PTK7 was expressed in human umbilical vascular endothelial cells (HUVECs), and the PTK7 expression was increased in a process of capillary-like tube formation on a surface of Matrigel. On the other hand, it was confirmed that when inhibiting PTK7 function, vascular endothelial cell migration induced by VEGF was reduced, and angiogenesis in vitro and in vivo was inhibited (Biochem. Biophys. Res. Commun., 2008; 371:793-8). In addition, in the human umbilical cord vascular endothelial cells, PTK7 oligomerizes a kinase insert domain receptor (KDR), one of VEGF receptors, to promote activation, thereby increasing KDR phosphorylation and promoting the vascular endothelial cell migration and the angiogenesis in vitro and in vivo (Biochim. Biophys. Acta, 2015; 1853: 2251-60). However, when PTK7 was present at a high concentration, PTK7 encloses KDR molecules, thereby inhibiting KDR activity.

Figure 10:
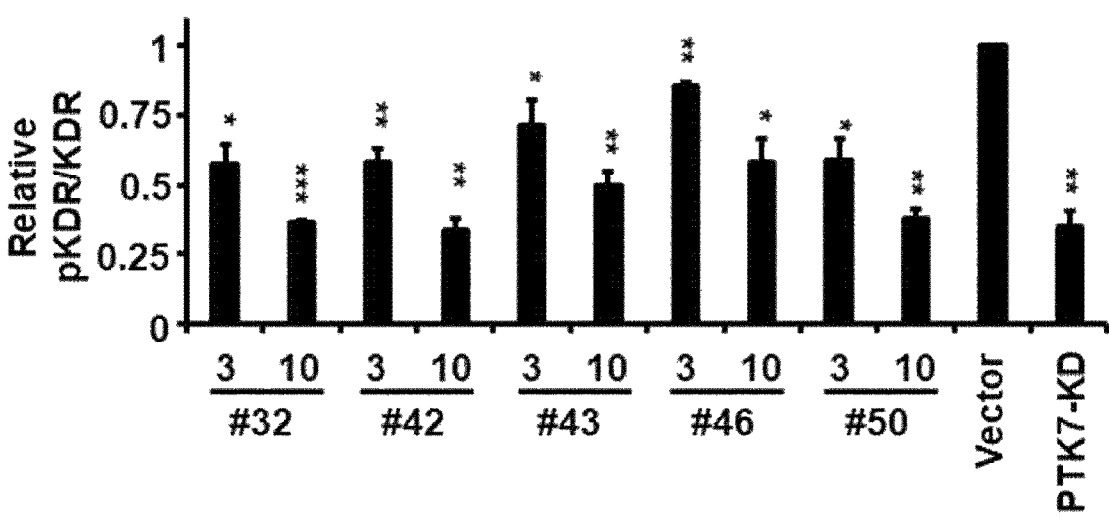
FIG. 10 is a diagram showing the inhibitory effect of VEGF-induced KDR phosphorylation by each of five types of PTK7 neutralizing monoclonal antibodies selected in the present invention at a concentration of 3 μg/ml or 10 μg/ml in HEK293 cells overexpressing KDR (*P<0.05, P<0.01, *P<0.001 vs. Vector. N=3)

Hence, based on the above results, the inventors analyzed the influence on VEGF-induced KDR phosphorylation and cell migration in HEK293 cells overexpressing KDR (HEK293-KDR). More specifically, the HEK293-KDR cells were treated with the five types of PTK7 monoclonal antibodies finally selected in Example 4 at a concentration of 3 μg/ml or 10 μg/ml to analyze the degree of KDR phosphorylation induced by 10 ng/ml VEGF. As a result, as shown in FIG. 10, when being treated with each of the antibodies at a concentration of 3 μg/ml, it was confirmed that the degree of inhibiting the KDR phosphorylation was exhibited in the order of 32>42>50>43>46. When being treated with each of the antibodies at a concentration of 10 μg/ml, the degree of inhibiting the KDR phosphorylation was exhibited in the order of 42>32>50>43>46.

Figure 11:
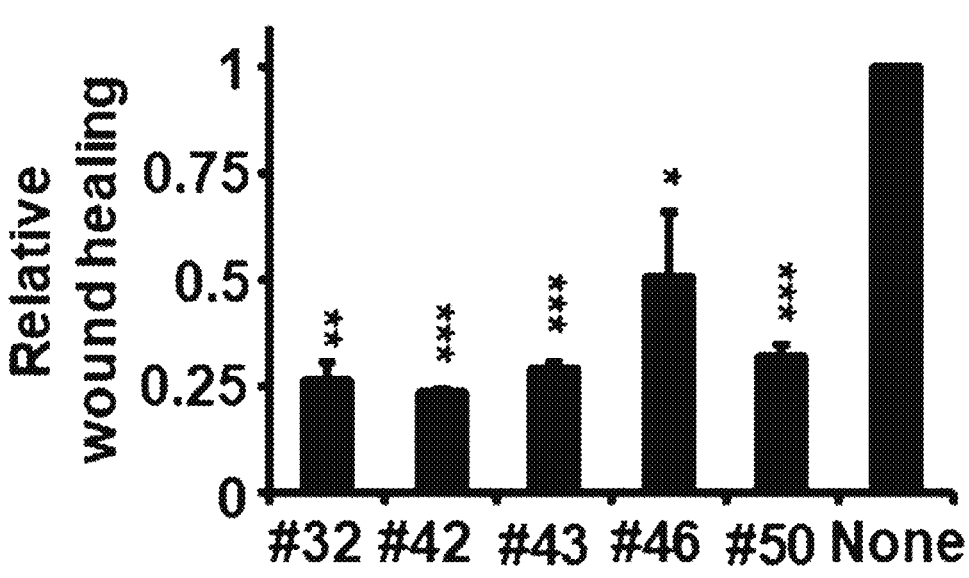
FIG. 11 is a diagram showing the inhibitory effect of VEGF-induced cell migration measured by wound healing by each of five types of PTK7 neutralizing monoclonal antibodies selected in the present invention at a concentration of 5 g/ml in HEK293 cells overexpressing KDR (*P<0.05, P<0.01, *P<0.001 vs. None. N=3)

In addition, based on the above results, the five types of the neutralizing monoclonal antibodies were added at a concentration of 5 μg/ml to the HEK293-KDR cells to analyze the inhibitory effect on VEGF-induced cell migration, which was measured by wound healing. As a result, as shown in FIG. 11, it was seen that the inhibitory effect on the cell migration was exhibited in the order of 42>32>43>50>46.

When considering the above results together, the PTK7 neutralizing antibody 46 was poor in inhibiting the oncogenic phenotypes of the esophageal squamous cell carcinoma cells and the triple-negative breast cancer cells at a low concentration (see Examples 3-2 and 4). In addition, the inhibitory effect of the PTK7 neutralizing antibody 46 at a low concentration on the angiogenic signaling and cell migration was also the lowest (see Example 5). Therefore, the four types of the PTK7 neutralizing antibodies 32, 42, 43, and 50, with excellent anti-cancer and anti-angiogenic efficacies, were finally selected.

Example 6. Analysis of Sequence for Complementarity-Determining Regions (CDRs) of PTK7 Neutralizing Monoclonal Antibodies An amino acid sequence of a hypervariable region of a heavy chain and light chain of an antibody, that is, an immunoglobulin (Ig), is called a complementarity-determining region (CDR). A CDR sequence of Ig provides important contact residues for the antibody binding to an antigen, and there are three CDRs in each of the heavy chain and the light chain.

Hence, to investigate the CDR sequences of the four types of the PTK7 neutralizing monoclonal antibodies finally selected through the results of the above examples, the inventors isolated total RNA from hybridoma cells secreting the antibodies, synthesized cDNA with oligo-dT$_{15}$ and a random hexamer, and then PCR-amplified with a primer set for an Ig hypervariable region. The resulting PCR products were cloned to examine a sequence for each clone, and CDR nucleotide sequences and amino acid sequences were analyzed using IGBLAST Tool (https://www.ncbi.nlm.nih.gov/igblast/). The CDR amino acid sequences of the four types of the PTK7 neutralizing monoclonal antibodies, according to the present invention, derived through the analysis are shown in Table 1 below, and amino acid sequence information for the entire heavy-chain variable regions and light-chain variable regions is shown in FIG. 12.

TABLE 1

| PTK7 mAb | Part | Amino acid sequence (N-C) | SEQ ID NO |
|---|---|---|---|
| #32 | CDR1_VH | GFDFSRYW | 1 |
| | CDR2_VH | INPDSSTI | 2 |
| | CDR3_VH | ARAYYIYYFDY | 3 |
| | CDR1_VL | QSLLYSSNQKNY | 4 |
| | CDR2_VL | WAS | 5 |
| | CDR3_VL | QQYYSYPWT | 6 |
| #42 | CDR1_VH | GYTFTNYG | 7 |
| | CDR2_VH | INTYTGEP | 8 |
| | CDR3_VH | AREEVGFPY | 9 |
| | CDR1_VL | QSLVHSNGNTY | 10 |
| | CDR2_VL | KVS | 11 |
| | CDR3_VL | SQSTHVPWT | 12 |
| #43 | CDR1_VH | GFNIKDTY | 13 |
| | CDR2_VH | IDPANGNT | 14 |
| | CDR3_VH | ARGDANYGAY | 15 |
| | CDR1_VL | ESVDNYGISF | 16 |
| | CDR2_VL | AAS | 17 |
| | CDR3_VL | QQSKEVPLT | 18 |
| #50 | CDR1_VH | GFDFSRYW | 19 |
| | CDR2_VH | INPDSSTI | 20 |
| | CDR3_VH | ARMELLWYFDV | 21 |
| | CDR1_VL | QSLLYSSNQKNY | 22 |
| | CDR2_VL | WAS | 23 |
| | CDR3_VL | QQYYSYPWT | 24 |

Example 7. Analysis of Antigen-Binding Sites of PTK7 Neutralizing Monoclonal Antibodies Antigen (sPTK7)-binding sites of each of the four types of the PTK7 neutralizing monoclonal antibodies that were finally selected in Example 5 were analyzed.

An extracellular region of PTK7 has 7 Ig loops (J. Biochem., 1996; 119 (2): 235-9). To analyze the antigen (sPTK7)-binding sites (Ig loops) of the four types of PTK7 neutralizing monoclonal antibodies that were finally selected, the entire extracellular region of PTK7 with a C-terminal His-tag (PTK7-Ext-His; also called as sPTK7; Ala31-Gln703+hexa-His) and mutant polypeptides with a portion of the extracellular region of PTK7, PTK7-Ig15-His (Ala31-Gly528+hexa-His), PTK7-Ig14-His (Ala31-Ala409+hexa-His), PTK7-Ig13-His (Ala31-Leu344+hexa-His), PTK7-Ig24-His (Ala31-Gln37+Trp123-Ala409+hexa-His), and PTK7-Ig34-His (Ala31-Gln37+Asp221-Ala409+hexa-His), were constructed, expressed, and purified.

Each of the six types of the PTK7 extracellular regions (PTK7-Ext-His, PTK7-Ig15-His, PTK7-Ig14-His, PTK7-Ig13-His, PTK7-Ig24-His, and PTK7-Ig34-His) bound to each of the PTK7 neutralizing antibodies, and then immunoprecipitation was performed to analyze whether the PTK7 extracellular region and the PTK7 neutralizing antibody bound to each other using western blotting.

Figure 13A:
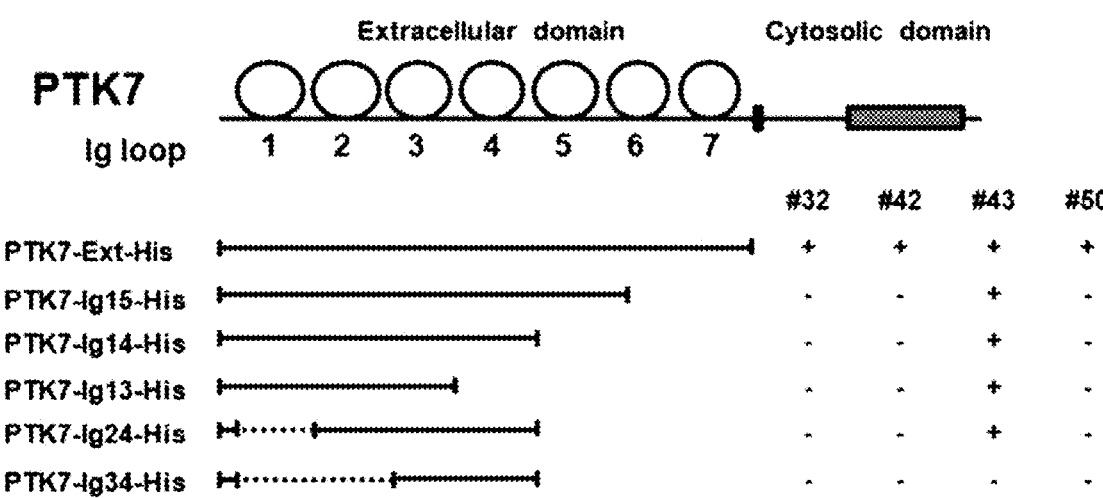
FIG. 13A is a schematic diagram showing binding of four types of PTK7 neutralizing monoclonal antibodies, according to the present invention, to sPTK7 (PTK7-Ext-His) and deletion mutants thereof.
Figure 13B:
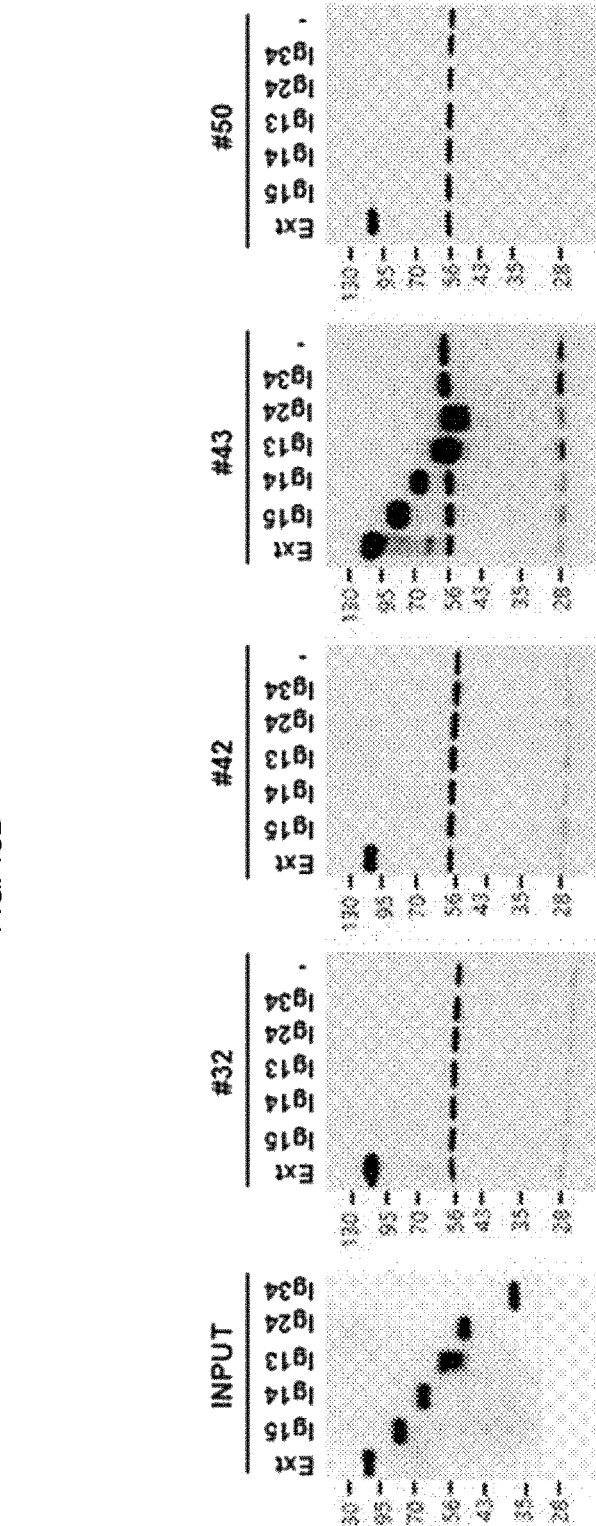
FIG. 13B is a diagram showing the immunoprecipitation analysis for the binding of four types of PTK7 neutralizing monoclonal antibodies, according to the present invention, to sPTK7 (PTK7-Ext-His) and deletion mutants thereof.

As a result, as shown in FIG. 13, it was seen that the PTK7 neutralizing antibody #43 bound to PTK7-Ext-His, PTK7-Ig15-His, PTK7-Ig14-His, PTK7-Ig-13-His, and PTK7-Ig-24-His, but not to PTK7-Ig34, thereby recognizing an Ig2 region (Trp123-Ala220). In addition, it was seen that the PTK7 neutralizing antibodies #32, #42, and #50 bound to PTK7-Ext-His, but not to other fragments, thereby recognizing an Ig67 region (Arg529-Gln703).

The above description of the present invention is given by way of illustration only, and it should be understood by those skilled in the art to which the present invention belongs that various changes and modifications can be made without departing from the technical spirit and scope of the present invention. Therefore, it should be understood that the aforementioned embodiments are given by way of illustration only, and are not intended to be limiting in all aspects.

INDUSTRIAL APPLICABILITY

Four types of human PTK7 neutralizing monoclonal antibodies, according to the present invention, have been confirmed to independently exhibit effective inhibitory effects on cancer cell growth, migration, and invasion in esophageal squamous cell carcinoma and triple-negative breast cancer and on angiogenesis. Therefore, the PTK7 neutralizing monoclonal antibodies can be further developed as a targeted drug therapy for various PTK7-positive carcinomas and angiogenic diseases. In addition, the PTK7 neutralizing monoclonal antibodies can be converted into humanized antibodies, and can be thus used as essential materials in developing a new drug capable of being clinically used. As a result, the PTK7 neutralizing monoclonal antibodies can be used not only solely but also in combination with other drugs, such as existing anti-cancer drugs that are proven to be effective, to maximize anti-cancer treatment effects, and can be widely used in the field of the treatment of intractable cancers and angiogenic diseases.

This application contains references to amino acid sequences and/or nucleic acid sequences which have been submitted concurrently herewith as the sequence listing text file entitled "000050usnp_SequenceListing.TXT", file size 20 kilobytes (KB), created on 13 Jul. 2023. The aforementioned sequence listing is hereby incorporated by reference in its entirety pursuant to 37 C.F.R. § 1.52(e)(5).

What is claimed is:

1. An anti-PTK7 antibody or a functional fragment thereof, the anti-PTK7 antibody or the functional fragment thereof specifically binding to protein tyrosine kinase 7 (PTK7) and comprising a heavy-chain variable region (HCVR) and a light-chain variable region (LCVR) selected from the group consisting of:

(i) a HCVR comprising a CDR1-VH having the amino acid sequence as set forth in SEQ ID NO: 1, a CDR2-VH having the amino acid sequence set forth in SEQ ID NO: 2, a CDR3-VH having the amino acid sequence set forth in SEQ ID NO: 3, and a LCVR comprising a CDR1-VL having the amino acid sequence as set forth in SEQ ID NO: 4, a CDR2-VL having the amino acid sequence set forth in SEQ ID NO: 5, a CDR3-VL having the amino acid sequence set forth in SEQ ID NO: 6;

(ii) a HCVR comprising a CDR1-VH having the amino acid sequence as set forth in SEQ ID NO: 7, a CDR2-VH having the amino acid sequence set forth in SEQ ID NO: 8, a CDR3-VH having the amino acid sequence set forth in SEQ ID NO: 9, and a LCVR comprising a CDR1-VL having the amino acid sequence as set forth in SEQ ID NO: 10, a CDR2-VL having the amino acid sequence set forth in SEQ ID NO: 11, a CDR3-VL having the amino acid sequence set forth in SEQ ID NO: 12;

(iii) a HCVR comprising a CDR1-VH having the amino acid sequence as set forth in SEQ ID NO: 13, a CDR2-VH having the amino acid sequence set forth in SEQ ID NO: 14, a CDR3-VH having the amino acid sequence set forth in SEQ ID NO: 15, and a LCVR comprising a CDR1-VL having the amino acid sequence as set forth in SEQ ID NO: 16, a CDR2-VL having the amino acid sequence set forth in SEQ ID NO: 17, a CDR3-VL having the amino acid sequence set forth in SEQ ID NO: 18; and (iv) a HCVR comprising a CDR1-VH having the amino acid sequence as set forth in SEQ ID NO: 19, a CDR2-VH having the amino acid sequence set forth in SEQ ID NO: 20, a CDR3-VH having the amino acid sequence set forth in SEQ ID NO: 21, and a LCVR comprising a CDR1-VL having the amino acid sequence as set forth in SEQ ID NO: 22, a CDR2-VL having the amino acid sequence set forth in SEQ ID NO: 23, a CDR3-VL having the amino acid sequence set forth in SEQ ID NO: 24.

2. The antibody or the functional fragment of claim 1, wherein the antibody or the functional fragment comprises a heavy-chain variable region with an amino acid sequence of SEQ ID NO: 25 and a light-chain variable region with an amino acid sequence of SEQ ID NO: 26.

3. The antibody or the functional fragment of claim 1, wherein the antibody or the functional fragment comprises a heavy-chain variable region with an amino acid sequence of SEQ ID NO: 27 and a light-chain variable region with an amino acid sequence of SEQ ID NO: 28.

4. The antibody or the functional fragment of claim 1, wherein the antibody or the functional fragment comprises a heavy-chain variable region with an amino acid sequence of SEQ ID NO: 29 and a light-chain variable region with an amino acid sequence of SEQ ID NO: 30.

5. The antibody or the functional fragment of claim 1, wherein the antibody or the functional fragment comprises a heavy-chain variable region with an amino acid sequence of SEQ ID NO: 31 and a light-chain variable region with an amino acid sequence of SEQ ID NO: 32.

6. The antibody or the functional fragment of claim 1, wherein the antibody or the functional fragment specifically binds to an extracellular region of PTK7 protein.

7. The antibody or the functional fragment of claim 1, wherein the antibody is selected from the group consisting of IgG, IgA, IgM, IgE, and IgD, and the functional fragment is selected from the group consisting of a diabody, Fab, F(ab'), F(ab')2, Fv, dsFv, and scFv.

8. The antibody or the functional fragment of claim 1, wherein a PTK7 antigen-binding site of the antibody is an Ig loop.

9. The antibody or the functional fragment of claim 1, wherein the Ig loop is an Ig2 region (Trp123-Ala220) represented by SEQ ID NO: 43 or an Ig67 region (Arg529-Gln703) represented by SEQ ID NO: 44.

10. A polynucleotide encoding the antibody or the functional fragment of claim 1.

11. A vector comprising the polynucleotide of claim 10.

12. A cell transformed to the vector of claim 11.

13. A method of producing an antibody specifically binding to PTK7 or a functional fragment thereof, the method comprising:

producing a polypeptide comprising a light-chain variable region and a heavy-chain variable region by culturing the cells of claim 12; and collecting the polypeptide from the cells or a culture medium of the cells.

14. An angiogenesis inhibitor comprising the anti-PTK7 antibody or the functional fragment of claim 1 as an active ingredient.

15. An inhibitor for tumor cell growth, migration, or invasion, the inhibitor comprising the anti-PTK7 antibody or the functional fragment of claim 1 as an active ingredient.

16. A pharmaceutical composition, the composition comprising the angiogenesis inhibitor of claim 14 as an active ingredient.

* * * * *